United States Patent [19]

Lok et al.

[11] Patent Number: 4,551,236
[45] Date of Patent: Nov. 5, 1985

[54] CONVERSION PROCESSES WITH TITANIUM-CONTAINING MOLECULAR SIEVES

[75] Inventors: Brent M. T. Lok, New City; Bonita K. Marcus, Rye; Edith M. Flanigen, White Plains, all of N.Y.

[73] Assignee: Union Carbide Corporation, Danbury, Conn.

[21] Appl. No.: 627,515

[22] Filed: Jul. 3, 1984

Related U.S. Application Data

[62] Division of Ser. No. 480,738, Mar. 31, 1983, Pat. No. 4,500,651.

[51] Int. Cl.$^4$ ............ C10G 11/04; C10G 11/05; C10G 45/12; C10G 47/04
[52] U.S. Cl. ................... 208/112; 208/114; 208/213; 208/216 R; 208/254 H; 208/135; 208/143; 585/440; 585/466; 585/470; 585/480; 585/486; 585/528; 585/646; 585/653; 585/667; 585/708; 585/725; 585/740
[58] Field of Search .......... 208/112, 114, 213, 216 R, 208/254 H

[56] References Cited

U.S. PATENT DOCUMENTS

| | | | |
|---|---|---|---|
| 3,448,164 | 6/1969 | Holm et al. | 502/208 |
| 4,310,440 | 1/1982 | Wilson et al. | 502/208 |
| 4,358,397 | 11/1982 | Chu | 585/467 |
| 4,382,854 | 5/1983 | Wilson et al. | 208/216 R |

FOREIGN PATENT DOCUMENTS 38479 10/1981 European Pat. Off. .
2071071 9/1981 United Kingdom .

OTHER PUBLICATIONS

Can Ti$^{4+}$ replace Si$^{4+}$ in Silicates?, Mineralogical magazine, Sep., vol. 37, No. 287, pp. 366–369, (1969).

Primary Examiner—D. E. Gantz
Assistant Examiner—O. Chaudhuri
Attorney, Agent, or Firm—Gary L. Warner

[57] ABSTRACT

Titanium-containing molecular sieves are disclosed having use as molecular sieves and as catalyst compositions in hydrocarbon conversion and other processes. The instant invention employs novel titanium-containing molecular sieves comprising titanium, aluminum, phosphorus and oxygen and are generally employable in hydrocarbon conversion processes, including cracking, hydrocracking and hydrotreating.

27 Claims, 3 Drawing Figures

CONVERSION PROCESSES WITH TITANIUM-CONTAINING MOLECULAR SIEVES

This application is a division of prior U.S. application Ser. No. 480,738, filed Mar. 31, 1983, now U.S. Pat. No. 4,500,651.

FIELD OF THE INVENTION

The present invention relates to a class of crystalline microporous molecular sieves to the method for their preparation, and to their use as adsorbents and catalysts. These compositions are prepared hydrothermally from gels containing reactive phosphorus, aluminum and titanium compounds and an organic templating agent(s).

BACKGROUND OF THE INVENTION

The existence of molecular sieves of the crystalline aluminosilicate type are well known to the art with numerous species having been found, both as naturally occurring materials and as synthetically formed materials. Numerous instances of the existence of these materials may be found in the art relating thereto and such will not be discussed herein.

The existence of crystalline microporous compositions which are other than zeolites, i.e., other than aluminosilicates, have been reported heretofore. For example, U.S. Pat. No. 4,310,440 discloses a novel family of crystalline, microporous crystalline aluminophosphate compositions.

Further, numerous patents have been obtained in compositions wherein metal and non-metal oxides have been deposited on an aluminosilicate. For example, U.S. Pat. No. 4,358,397 discloses a modified zeolite (aluminosilicate) which has been modified to have at least 0.25 weight percent of one or more Group IV A metals incorporated into the zeolite in the oxide form and at least 0.25 weight percent of phosphorus incorporated into the zeolite in the oxide form of phosphorus. The term "incorporation" is clarified in column 2, beginning at line 8 as being a " . . . treatment with a compound derived from one or more elements of Group IV A of the Periodic Table of Elements (i.e., Ti, Zr and Hf) to yield a composite containing a minor proportion of an oxide of such element." Similarly, the zeolites are disclosed as being treated with a phosphorus-containing compound to deposit a minor proportion of an oxide of phosphorus.

Although there has been an extensive treatment in the patent art and in the published literature of aluminosilicates and recently, aluminophosphates, there has been little information available on the presence of other than such materials. This is particularly true in the area of titanium containing compositions wherein titanium is present in the framework of the molecular sieve or so intimately related as to change the physical and/or chemical characteristics of the molecular sieve. This is understandable in the question of aluminosilicates, as indicated by the article, "Can Ti$^{4+}$ replace Si$^{4+}$ in silicates?", Mineralogical Magazine, September vol 37, No. 287, pages 366–369 (1969). In this article it is concluded that substitution of framework silicon by titanium does not usually occur in aluminosilicates owing to the preference of titanium to be octahedrally bound rather than tetrahedrally bound. The formation of crystalline "titanosilicate zeolites*" is disclosed in U.S. Pat. No. 3,329,481, wherein a metallo-silicate complex is formed and treated to give the titano silicate product. The evidence for the claimed titanosilicate is based on the X-ray power diffraction pattern data. The X-ray data are somewhat suspect as to whether such show substitution of titanium into the silicate framework inasmuch as the claimed X-ray patterns are also observed for the zirconium silicates and by the fact that similar X-ray patterns showing similar interplanar distances for the two values in patterns B) have been reported for silicalite. (See. G.B. Pat. No. 2,071,071 A).

*Obviously, the product is not a zeolite since it is not an aluminosilicate.

The incorporation of titanium in a silicalite type structure is disclosed in G.B. Pat. No. 2,071,071 A, published Dec. 21, 1979. The amount of titanium claimed to be substituted into the silicate-type structure is very small, being no more than 0.04 mole percent, based on the number of moles of silica, and may be as low as 0.0005. The titanium content was determined by chemical analysis and was not determined to be greater than 0.023 in any case. As indicated by a comparison of FIG. 1a and FIG. 1b, the amount of titanium present is small and no significant change in the X-ray diffraction pattern of silicalite was observed and the minor changes observed may simply be due to occluded titanium dioxide. Thus, absent other analytical data the results are not well defined. No comparison data for titanium dioxide are disclosed.

In view of the above, it is clear that the substitution of titanium into a zeolitic-type framework is conceived to be possible, wherein titanium substitutes for silicon, but difficult of proof. The substitution of titanium in non-zeolitic materials has not hereto been disclosed although a number of minerals have been found to contain titanium (see: "Can Ti Replace Si in Silicates", supra). Further, although titanium has been postulated to substitute for silicon in the aluminosilicate framework it has not heretofore been considered as to what occurs when silicon is not present. Specifically, these questions have not heretofore been considered in the art with respect to titanium substitution in aluminophosphate molecular sieves and such is the subject of the instant invention.

SUMMARY OF THE INVENTION

Figure 1:
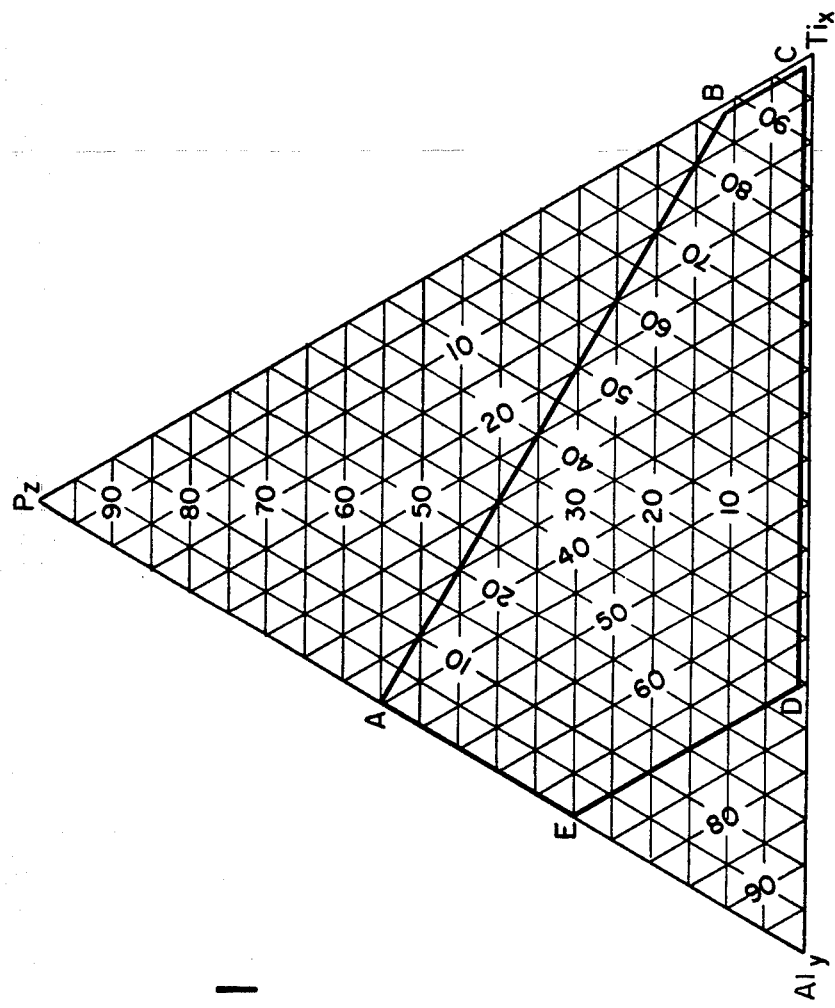
FIG. 1 is a ternary diagram showing the compositional parameters of the titanium-containing molecular sieves of this invention in terms of titanium, aluminum and phosphorus.

The present invention relates to titanium-containing molecular sieves comprising a three-dimensional microporous crystal framework structure of [TiO$_2$], [AlO$_2$] and [PO$_2$] tetrahedral units which has a unit empirical formula on an anhydrous basis of:

$$mR:(Ti_xAl_yP_z)O_2 \qquad (1)$$

wherein "R" represents at least one organic templating agent present in the intracrystalline pore system; "m" represents the moles of "R" present per mole of $(Ti_xAl_yP_z)O_2$ and has a value of between zero and about 5.0., the maximum value in each case depending upon the molecular dimensions of the templating agent and the available void volume of pore system of the particular titanium molecular sieve; "x", "y" and "z" represent the mole fractions of titanium, aluminum and phosphorus, respectively, present as tetrahedral oxides, said mole fractions being such that they are within the pentagonal compositional area defined by points A, B, C, D and E of the ternary, said diagram which is FIG. 1 of the drawings, points A, B, C, D and E representing the following values for "x", "y" and "z":

| Point | Mole Fraction | | |
|-------|------|------|------|
|       | x    | y    | z    |
| A     | 0.001 | 0.45 | 0.549 |
| B     | 0.88 | 0.01 | 0.11 |
| C     | 0.98 | 0.01 | 0.01 |
| D     | 0.29 | 0.70 | 0.01 |
| E     | 0.001 | 0.70 | 0.299 |

Figure 2:
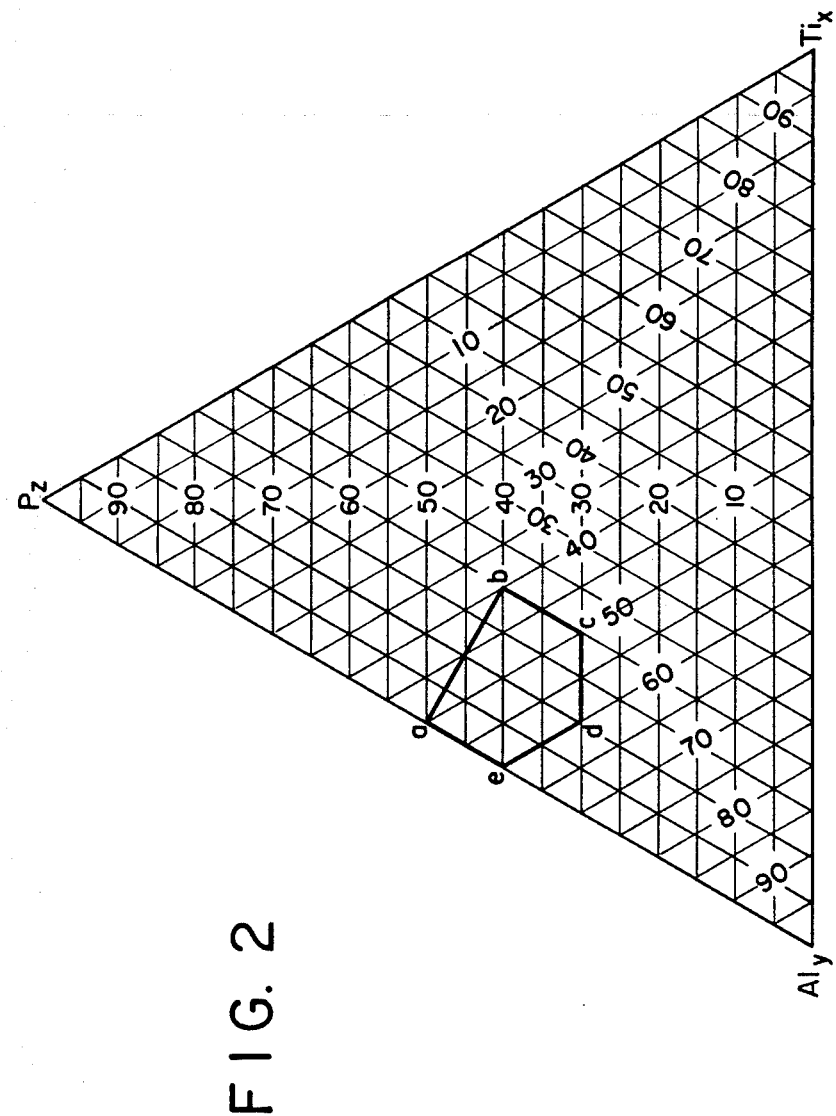
FIG. 2 is a ternary diagram showing preferred compositional parameters of the titanium-containing molecular sieves of this invention in terms of titanium, aluminum and phosphorus.

The parameters of "x", "y" and "z" are preferably within the pentagonal compositional area defined by points a, b, c, d and e of the ternary diagram which is FIG. 2 of the drawings, said points a, b, c, d and e representing the following values for "x", "y" and "z":

| Point | Mole Fraction | | |
|-------|------|------|------|
|       | x    | y    | z    |
| a     | 0.002 | 0.499 | 0.499 |
| b     | 0.20 | 0.40 | 0.40 |
| c     | 0.20 | 0.50 | 0.30 |
| d     | 0.10 | 0.60 | 0.30 |
| e     | 0.002 | 0.60 | 0.398 |

The molecular sieves of the present invention are generally employable as catalysts for various hydrocarbon conversion processes.

DETAILED DESCRIPTION OF THE INVENTION

The present invention relates to titanium-containing molecular sieves comprising a three-dimensional microporous crystal framework structure of $[TiO_2]$, $[AlO_2]$ and $[PO_2]$ tetrahedral units which has a unit empirical formula on an anhydrous basis of:

$$mR:(Ti_xAl_yP_z)O_2 \qquad (1)$$

wherein "R" represents at least one organic templating agent present in the intracrystalline pore system; "m" represents the moles of "R" present per mole of $(Ti_xAl_yP_z)O_2$ and has a value of between zero and about 5.0., the maximum value in each case depending upon the molecular dimensions of the templating agent and the available void volume of pore system of the particular titanium molecular sieve, "x", "y" and "z" represent the mole fractions of titanium, aluminum and phosphorus, respectively, present as tetrahedral oxides, said mole fractions being such that they are within the pentagonal compositional area defined by points A, B, C, D and E representing the following values for "x", "y" and "z":

| Point | Mole Fraction | | |
|-------|------|------|------|
|       | x    | y    | z    |
| A     | 0.001 | 0.45 | 0.549 |
| B     | 0.88 | 0.01 | 0:11 |
| C     | 0.98 | 0.01 | 0.01 |
| D     | 0.29 | 0.70 | 0.01 |
| E     | 0.001 | 0.70 | 0.299 |

The parameters "x", "y" and "z" are preferably within the pentagonal compositional area defined by points a, b, c, d and e of the ternary diagram which is FIG. 2 of the drawings, said points a, b, c, d and e representing the following values for "x", "y" and "z":

| Point | Mole Fraction | | |
|-------|------|------|------|
|       | x    | y    | z    |
| a     | 0.002 | 0.499 | 0.499 |
| b     | 0.20 | 0.40 | 0.40 |
| c     | 0.20 | 0.50 | 0.30 |
| d     | 0.10 | 0.60 | 0.30 |
| e     | 0.002 | 0.60 | 0.398 |

The molecular sieves of the present invention are generally employable as catalysts for various hydrocarbon conversion processes.

The molecular sieves employed in the instant process will be referred to hereinafter, solely for point of reference herein as "TAPO" molecular sieves, or as "TAPOs" if the reference is to the class as a whole. This designation is simply made for the sake of convenient reference herein and is not meant to designate a particular structure for any given TAPO molecular sieve. The members of the class of TAPO's employed hereinafter in the examples will be characterized simply by referring to such members as TAPO-5, TAPO-11, etc, i.e., a particular species will be referred to as TAPO-n where "n" is a number specific to a given class member as its preparation is reported herein. This designation is an arbitrary one and is not intended to denote structural relationship to another material(s) which may also be characterized by a numbering system.

The term "unit empirical formula" is used herein according to its common meaning to designate the simplest formula which gives the relative number of moles of titanium, aluminum and phosphorus which form the $[TiO_2]$, $[PO_2]$ and $[AlO_2]$ tetrahedral unit within a titanium-containing molecular sieve and which forms the molecular framework of the TAPO composition(s). The unit empirical formula is given in terms of titanium, aluminum and phosphorus as shown in Formula (1), above, and does not include other compounds, cations or anions which may be present as a result of the preparation or the existence of other impurities or materials in the bulk composition not containing the aforementioned tetrahedral unit. The amount of template R is reported as part of the composition when the as-synthesized unit empirical formula is given, and water may also be reported unless such is defined as the anhydrous form. For convenience, coefficient "m" for template "R" is reported as a value that is normalized by dividing the number of moles of organic by the total moles of titanium, aluminum and phosphorus.

The unit empirical formula for a given TAPO can be calculated using the chemical analysis data for that TAPO. Thus, for example, in the preparation of TAPO-11 disclosed hereinafter in Example 9, the over all composition of the as-synthesized TAPO-11 is calculated using the chemical analysis data and expressed in terms of molar oxide ratios on an anhydrous basis are: $0.29(n(Pr)NH):0.095Al_2O_3:0.3TiO_2:0.92P_2O_5$. The unit empirical formula for the as-synthesized TAPO-11 composition on an anhydrous basis is: $0.074(n(Pr)NH):(Ti_{0.024}Al_{0.508}P_{0.468})O_2$ using the aforementioned formula form of $$mR:(Ti_xAl_yP_z)O_2$$

This unit empirical as-synthesized formula is readily computed from the molar oxide ratio expression in which the components [n(Pr)NH], Ti, Al and P are present in the molar ratio of:

$$0.29R:0.095Ti:2.0Al:1.84P$$

The sum $(Ti+Al+P)=(0.095+2.0+1.84)=3.935$ normalized to $(Ti+Al+P)=1.00$ by dividing each term by 3.935, thusly: $m=(0.29/3.935)=0.074$; $x=(0.095/3.935)=0.024$; $y=(2.0/3.935)=0.508$; and $z=(1.84/3.935)=0.468$.

The unit empirical formula for a TAPO may be given on an "as-synthesized" basis or may be given after an "as-synthesized" TAPO composition has been subjected to some post treatment process, e.g., calcination. The term "as-synthesized" herein shall be used to refer to the TAPO composition(s) formed as a result of the hydrothermal crystallization but before the TAPO composition has been subjected to post treatment to remove any volatile components present therein. The actual value of "m" for a post-treated TAPO will depend on several factors (including: the particular TAPO, template, severity of the post-treatment in terms of its ability to remove the template from the TAPO, the proposed application of the TAPO composition, and etc.) and the value for "m" can be within the range of values as defined for the as-synthesized TAPO compositions although such is generally less than the as-synthesized TAPO unless such post-treatment process adds template to the TAPO so treated. A TAPO composition which is in the calcined or other post-treatment form generally has an empirical formula represented by Formula (1), except that the value of "m" is generally less than about 0.02. Under sufficiently severe post-treatment conditions, e.g. roasting in air at high temperature for long periods (over 1 hr.), the value of "m" may be zero (0) or, in any event, the template, R, is undetectable by normal analytical procedures.

The molecular sieves of the present invention are generally further characterized by an intracrystalline adsorption capacity for water at 4.6 torr and about 24° C. of about 3.0 weight percent. The adsorption of water has been observed to be completely reversible while retaining the same essential framework topology in both the hydrated and dehydrated state. The term "essential framework topology" is meant to designate the spatial arrangement of the primary bond linkages. A lack of change in the framework topology indicates that there is no disruption of these primary bond linkages.

The molecular sieves of the instant invention are generally synthesized by hydrothermal crystallization from a reaction mixture comprising reactive sources of titanium, aluminum and phosphorus, and one or more organic templating agents. Optionally, alkali metal(s) may be present in the reaction mixture. The reaction mixture is placed in a pressure vessel, preferably lined with an inert plastic material, such as polytetrafluoroethylene, and heated, preferably under the autogenous pressure, at a temperature of at least about 100° C., and preferably between 100° C. and 250° C., until crystals of the molecular sieve product are obtained, usually for a period of from 2 hours to 2 weeks. While not essential to the synthesis of the instant molecular sieves, it has been found that in general stirring or other moderate agitation of the reaction mixture and/or seeding the reaction mixture with seed crystals of either the TAPO to be produced, or a topologically similar composition, facilitates the crystallization procedure. The product is recovered by any convenient method such as centrifugation or filtration.

After crystallization the TAPO may be isolated and washed with water and dried in air. As a result of the hydrothermal crystallization, the as-synthesized TAPO contains within its intracrystalline pore system at least one form of the template employed in its formation. Generally, the template is a molecular species, but it is possible, steric considerations permitting, that at least some of the template is present as a charge-balancing cation. Generally the template is too large to move freely through the intracrystalline pore system of the formed TAPO and may be removed by a post-treatment process, such as by calcining the TAPO at temperatures of between about 200° C. and to about 700° C. so as to thermally degrade the template or by employing some other post-treatment process for removal of at least part of the template from the TAPO. In some instances the pores of the TAPO are sufficiently large to permit transport of the template, and, accordingly, complete or partial removal thereof can be accomplished by conventional desorption procedures such as carried out in the case of zeolites.

Figure 3:
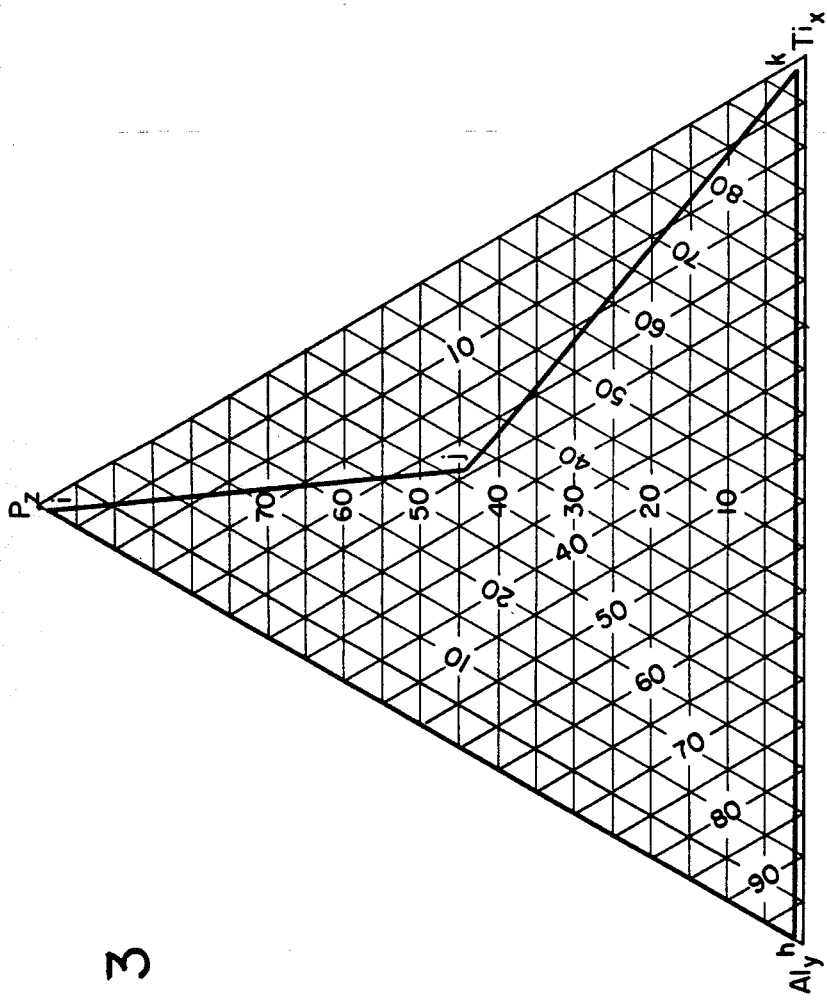
FIG. 3 is a ternary diagram showing the compositional parameters of the reaction mixtures used to prepare the titanium-containing molecular sieves of this invention in terms of titanium, aluminum and phosphorus.

The TAPOs are preferably formed from a reaction mixture having a mole fraction of alkali metal cation which is sufficiently low that it does not interfere with the formation of the TAPO composition. The TAPO compositions are generally formed from a reaction mixture containing reactive sources of $TiO_2$, $Al_2O_3$, and $P_2O_5$ and an organic templating agent, said reaction mixture comprising a composition expressed in terms of molar oxide ratios of:

$$fR_2O:(Ti_xAl_yP_z)O_2:gH_2O$$

wherein "R" is an organic templating agent; "f" has a value large enough to constitute an effective amount of "R" said effective amount being that amount which form said TAPO compositions; "g" has a value of from zero to 500; "x", "y" and "z" represent the mole fractions, respectively of titanium, aluminum and phosphorus in the $(Ti_xAl_yP_z)O_2$ constituent, and each has a value of at least 0.001 and being within the quadrilateral compositional area defined by points, h, i, j and k which is FIG. 3 of the drawings, said points h, i, j and k representing the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

Although the TAPO compositions will form if higher concentrations of alkali metal cation are present, such reaction mixtures are not generally preferred. A reaction mixture, expressed in terms of molar oxide ratios, comprising the following bulk composition is preferred:

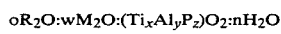

wherein "R" is an organic template; "o" has a value great enough to constitute an effective concentration of "R" and is preferably within the range of from greater than zero (0) to about 5.0; "M" is an alkali metal cation; "w" has a value of from zero to 2.5; "n" has a value between about zero (0) and about 500; "x", "y" and "z" represent the mole fractions, respectively of titanium, aluminum and phosphorus in the $(Ti_xAl_yP_z)O_2$ constituent, and each has a value of at least 0.001 and being within the quadtrilateral compositional area defined by points, h, i, j and k which is FIG. 3 of the drawings, said points h, i, j and k representing the following values for "x", "y" and "z":

| Point | Mole Fraction | | |
|---|---|---|---|
| | x | y | z |
| h | 0.001 | 0.989 | 0.01 |
| i | 0.001 | 0.01 | 0.989 |
| j | 0.32 | 0.24 | 0.44 |
| k | 0.98 | 0.01 | 0.01 |

When the TAPOs are synthesized by this method the value of "m" in Formula (1) is generally above about 0.02.

Though the presence of alkali metal cations is not preferred, when they are present in the reaction mixture it is preferred to first admix at least a portion (e.g. at least 10 weight percent) of each of the aluminum and phosphorus sources in the substantial absence (e.g. preferably less than about 20 percent of the total weight of the aluminum source and phosphorus source) of the titanium source. This procedure avoids adding the phosphorus source to a basic reaction mixture containing the titanium source and aluminum source, (as was done in most of the published attempts to substitute isomorphously [$PO_2$] tetrahedra for [$SiO_2$] tetrahedra in zeolitic structures). Although the reaction mechanism is by no means clear at this time, the function of the template may be to favor the incorporation of [$PO_2$] and [$AlO_2$] tetrahedra in the framework structures of the crystalline products with [$TiO_2$] tetrahedra isomorphously replacing [$PO_2$] tetrahedra.

The reaction mixture from which these TAPOs are formed contain one or more organic templating agents (templates) which can be most any of those heretofore proposed for use in the synthesis of aluminosilicates and aluminophosphates. The template preferably contains at least one element of Group VA of the Periodic Table, particularly nitrogen, phosphorus, arsenic and/or antimony, more preferably nitrogen or phosphorus and most preferably nitrogen and are of the formula $R_4X^+$ wherein X is selected from the group consisting of nitrogen, phosphorus, arsenic and/or antimony and R may be hydrogen, alkyl, aryl, aralkyl, or alkylaryl group and is preferably aryl or alkyl containing between 1 and 8 carbon atoms, although more than eight carbon atoms may be present in "R" of group of the template. Nitrogen-containing templates are preferred, including amines and quaternary ammonium compounds, the latter being represented generally by the formula $R'_4N^+$ wherein each $R'$ is an alkyl, aryl, alkylaryl, or aralkyl group; wherein $R'$ preferably contains from 1 to 8 carbon atoms or higher when $R'$ is alkyl and greater than 6 carbon atoms when $R'$ is otherwise, as hereinbefore discussed. Polymeric quaternary ammonium salts such as $[(C_{14}H_{32}N_2)(OH)_2]_x$ wherein "x" has a value of at least 2 may also be employed. The mono-, di- and tri-amines, including mixed amines, may also be employed as templates either alone or in combination with a quaternary ammonium compound or another template. The exact relationship of various templates when concurrently employed is not clearly understood. Mixtures of two or more templating agents can produce either mixtures of TAPOs or in the instance where one template is more strongly directing than another template the more strongly directing template may control the course of the hydrothermal crystallization wherein with the other template serving primarily to establish the pH conditions of the reaction mixture.

Representative templates include tetramethylammonium, tetraethylammonium, tetrapropylammonium or tetrabutylammonium ions; di-n-propylamine; tripropylamine; triethylamine; triethanolamine; piperidine; cyclohexylamine; 2-methylpyridine; N,N-dimethylbenzylamine; N,N-diethylethanolamine; dicyclohexylamine; N,N-dimethylethanolamine; 1,4-diazabicyclo (2,2,2) octane; N-methyldiethanolamine, N-methylethanolamine; N-methylcyclohexylamine; 3-methylpyridine; 4-methylpyridine; quinuclidine; N,N'-dimethyl-1,4-diazabicyclo (2,2,2) octane ion; di-n-butylamine, neopentylamine; di-n-pentylamine; isopropylamine; t-butylamine; ethylenediamine; pyrrolidine; and 2-imidazolidone. As will be readily apparent from the illustrative examples set forth hereinafter, not every template will product every TAPO composition although a single template can, with proper selection of the reaction conditions, cause the formation of different TAPO compositions, and a given TAPO composition can be produced using different templates.

In those instances where an aluminum alkoxide is the reactive aluminum source, the corresponding alcohol is necessarily present in the reaction mixture since it is a hydrolysis product of the alkoxide. It has not as yet been determined whether this alcohol participates in the synthesis process as a templating agent, or in some other function and, accordingly, is no reported as a template in the unit formula of the TAPOs, although such may be acting as templates.

Alkali metal cations if present in the reaction mixture may facilitate the crystallization of certain TAPO phases, although the exact function of such cations, when present, in crystallization, if any, is not presently known. Alkali cations present in the reaction mixture generally appear in the formed TAPO composition, either as occluded (extraneous) cations and/or as structural cations balancing net negative charges at various sites in the crystal lattice. It should be understood that although the unit formula for the TAPOs does not specifically recite the presence of alkali cations they are not excluded in the same sense that hydrogen cations and/or hydroxyl groups are not specifically provided for in the traditional formulae for zeolitic aluminosilicates.

Most any reactive titanium source may be employed herein. The preferred reactive titanium sources include titanium alkoxides, water-soluble titanates and titanium chelates.

Most any reactive phosphorus source may be employed. Phosphoric acid is the most suitable phosphorus source employed to date. Accordingly, other acids of phosphorus are generally believed to be suitable phosphorus sources for use herein. Organic phosphates such as triethyl phosphates have been found satisfactory, and so also have crystalline or amorphous aluminophosphates such as the AlPO$_4$ compositions of U.S. Pat. No. 4,310,440. Organo-phosphorus compounds, such as tetrabutyl-phosphonium bromide have not, apparently, served as reactive sources of phosphorus, but these compounds do function as templating agents and may also be capable of being suitable phosphorus sources under proper process conditions (yet to be ascertained). Organic phosphorus compounds, e.g. esters, are believed to be generally suitable since they can generate acids of phosphorus in situ. Conventional phosphorus salts, such as sodium metaphosphate, may be used, at least in part as the phosphorus source, but they are not preferred.

Most any reactive aluminum source may be employed herein. The preferred reactive aluminum sources include aluminum alkoxides, such as aluminum isopropoxide, and pseudoboehmite. Crystalline or amorphous aluminophosphates which are a suitable source of phosphorus are, of course, also suitable sources of aluminum. Other sources of aluminum used in zeolite sythesis, such as gibbsite, sodium aluminate and aluminum trichloride, can be employed but as generally not preferred.

Since the exact nature of the TAPO molecular sieves of the present invention are not clearly understood at present, although all are believed to contain [TiO$_2$] tetrahedra in the three-dimensional microporous crystal framework structure, it is advantageous to characterize the TAPO molecular sieves by means of their chemical composition. This is due to the low level of titanium present in certain of the instant molecular sieves prepared to date which makes it difficult to ascertain the exact nature of the interaction between titanium, aluminum and phosphorus. As a result, although it is believed that titanium, [TiO$_2$], has substituted isomorphously for [AlO$_2$] or [PO$_2$] tetrahedra, it is appropriate to characterize certain TAPO compositions by reference to their chemical composition in terms of the mole ratios of oxides in the as-synthesized and anhydrous form as:

$$vR:pTiO_2:qAl_2O_3:rP_2O_5$$

wherein "R" represents at least one organic templating agent present in the intracrystalline pore system; "v" represents an effective amount of the organic templating agent to form said TAPO compositions and preferably has a value between and including zero and about 3.0; "p", "q" and "r" represent moles, respectively, of titanium dioxide, alumina and phosphorus pentaoxide, based on said moles being such that they are within the pentagonal compositional area defined by point A, B, C, D and E of the ternary diagram which is FIG. 1 of the drawings, said points A, B, C, D and E representing the following values for "p", "q" and "r".

| Point | Mole | | |
|---|---|---|---|
| | p | q | r |
| A | 0.004 | 1.0 | 1.22 |
| B | 176 | 1.0 | 11.0 |
| C | 196 | 1.0 | 1.0 |

-continued

| Point | Mole | | |
|---|---|---|---|
| | p | q | r |
| D | 0.828 | 1.0 | 0.0143 |
| E | 0.003 | 1.0 | 0.427 |

The parameters "p", "q" and "r" are preferably within the pentagonal compositional area defined by points a, b, c, d and e of the ternary diagram which is FIG. 2 of the drawings, said points a, b, c, d and e representing the following values for "p", "q" and "r":

| Point | Mole | | |
|---|---|---|---|
| | p | q | r |
| a | 0.008 | 1.0 | 1.0 |
| b | 1.0 | 1.0 | 1.0 |
| c | 0.80 | 1.0 | 0.60 |
| d | 0.333 | 1.0 | 0.50 |
| e | 0.067 | 1.0 | 0.663 |

The TAPO compositions of this invention have unique surface characteristics making them useful as molecular sieves and as catalyst or as bases for catalysts in a variety of separation, hydrocarbon conversion and oxidative combustion processes. The TAPO composition can be impregnated or otherwise associated with catalytically active metals by the numerous methods known in the art and used, for example, in fabricating catalysts compositions containing alumina or aluminosilicate materials.

TAPO's may be employed for separating molecular species in admixture with molecular species of a different degree of polarity or having different kinetic diameters by contacting such mixtures with a TAPO(s) having pore diameters large enough to adsorb at least one but not all molecular species of the mixture based on the polarity of the adsorbed molecular species and/or its kinetic diameter. When TAPOs are employed for such separation processes the TAPOs are at least partially activated whereby some molecular species selectively enter the intracrystalline pore system thereof.

The hydrocarbon conversion reactions catalyzed by TAPO compositions include; cracking, hydrocracking; alkylation of both the aromatic and isoparaffin types, isomerization (including xylene isomerization); polymerization; reforming; hydrogenation; dehydrogenation; transalkylation; dealkylation; and hydration.

When a TAPO containing catalyst compositions contains a hydrogenation promoter, such promoter may be platinum, palladium, tungsten, nickel or molybdenum and may be used to treat various petroleum stocks including heavy petroleum residual stocks, cyclic stocks and other hydrocrackable charge stocks. These stocks can be hydrocracked at temperatures in the range of between about 400° F. and about 825° F. using molar ratios of hydrogen to hydrocarbon in the range of between about 2 and about 80, pressures between about 10 and about 3500 p.s.i.g., and a liquid hourly space velocity (LHSV) of between about 0.1 and about 20, preferably between about 1.0 and about 10.

TAPO containing catalyst compositions may also be employed in reforming processes in which the hydrocarbon feedstocks contact the catalyst at temperatures between about 700° F. and about 1000° F., hydrogen pressures of between about 100 and about 500 p.s.i.g., LHSV values in the range between about 0.1 and about 10 and hydrogen to hydrocarbon molar ratios in the range between about 1 and about 20, preferably between about 4 and about 12.

Further, TAPO containing catalysts which contain hydrogenation promoters, are also useful in hydroisomerization processes wherein the feedstock(s), such as normal paraffins, is converted to saturated branched-chain isomers. Hydroisomerization processes are typically carried out at a temperature between about 200° F. and about 600° F., preferably between about 300° F. and about 550° F. with an LHSV value between about 0.2 and about 1.0. Hydrogen is typically supplied to the reactor in admixture with the hydrocarbon feedstock in molar proportions of hydrogen to the feedstock of between about 1 and about 5.

TAPO-containing compositions similar to those employed for hydrocracking and hydroisomerization may also be employed at between about 650° F. and about 1000° F., preferably between about 850° F. and about 950° F. and usually at somewhat lower pressures within the range between about 15 and about 50 p.s.i.g. for the hydroisomerization of normal paraffins. Preferably the paraffin feedstock comprises normal paraffins having a carbon number range of $C_7-C_{20}$. The contact time between the feedstock and the TAPO containing catalyst is generally relatively short to avoid undersirable side reactions such as olefin polymerization and paraffin cracking. LHSV values in the range between about 0.1 and about 10, preferably between about 1.0 and about 6.0 are suitable.

The low alkali metal content (often not measurable by current analytical techniques) of the instant TAPO compositions make them particularly well suited for use in the conversion of alkylaromatic compounds, particularly for use in the catalytic disproportionation of toluene, xylene, trimethylbenzenes, tetramethylbenzenes and the like. In such disproportionation processes it has been observed that isomerization and transalkylation can also occur. The TAPO-containing catalysts for such processes will typically include Group VIII noble metal adjuvants alone or in conjunction with Group VI-B metals such as tungsten, molybdenum and chromium which are preferably included in such catalyst compositions in amounts between about 3 and about 15 weight-% of the overall catalyst composition. Extraneous hydrogen can, but need not be present in the reaction zone which is maintained at a temperature between about 400° and about 750° F., pressures in the range between about 100 and about 2000 p.s.i.g., and LHSV values in the range between about 0.1 and about 15.

TAPO containing catalysts may be employed in catalytic cracking processes wherein such are preferably employed with feedstocks such as gas oils, heavy naphthas, deasphalted crude oil residues etc. with gasoline being the principal desired product. Temperature conditions are typically between about 850° and about 1100° F., LHSV values between about 0.5 and about 10 pressure conditions are between about 0 p.s.i.g. and about 50 p.s.i.g.

TAPO containing catalysts may be employed for dehydrocyclization reactions which employ paraffinic hydrocarbon feedstocks, preferably normal paraffins having more than 6 carbon atoms, to form benzene, xylenes, toluene and the like. Dehydrocyclization processes are typically carried out using reaction conditions similar to those employed for catalytic cracking. For such processes it is preferred to use a Group VIII non-noble metal cation such as cobalt and nickel in conjunction with the TAPO composition.

TAPO containing catalysts may be employed in catalytic dealkylation where paraffinic side chains are cleaved from aromatic nuclei without substantially hydrogenating the ring structure at relatively high temperatures in the range between about 800° F. and about 1000° F. at moderate hydrogen pressures between about 300 and about 1000 p.s.i.g. with other conditions being similar to those described above for catalytic hydrocracking. TAPO containing catalysts for catalytic dealkylation are of the same type described above in connection with catalytic dehydrocyclization. Particularly desirable dealkylation reactions contemplated herein include the conversion of methylnaphthalene to naphthalene and toluene and/or xylenes to benzene.

TAPO containing catalysts may be used in catalytic hydrofining wherein the primary objective is to provide for the selective hydrodecomposition of organic sulfur and/or nitrogen compounds without substantially affecting hydrocarbon molecules present therewith. For this purpose it is preferred to employ the same general conditions described above for catalytic hydrocracking. The catalysts are the same typically of the same general nature as described in connection with dehydrocyclization operations. Feedstocks commonly employed for catalytic hydroforming include: gasoline fractions, kerosenes; jet fuel fractions; diesel fractions; light and heavy gas oils; deasphalted crude oil residua; and the like. The feedstock may contain up to about 5 weight-percent of sulfur and up to about 3 weight-percent of nitrogen.

TAPO containing catalysts may be employed for isomerization processes under conditions similar to those described above for reforming although isomerization processes tend to require somewhat more acidic catalysts than those employed in reforming processes. Olefins are preferably isomerized at temperatures between about 500° F. and about 900° F., while paraffins, naphthenes and alkyl aromatics are isomerized at temperatures between about 700° F. and about 1000° F. Particularly desirable isomerization reactions contemplated herein include the conversion of n-heptane and/or n-octane to isoheptanes, iso-octanes, butane to isobutane, methylcyclopentane to cyclohexane, meta-xylene and/or ortho-xylene to para-xylene, 1-butene to 2-butene and/or isobutene, n-hexene to isohexane, cyclohexane to methylcyclopentene etc. The preferred cation form is a combination of a TAPO with polyvalent metal compounds (such as sulfides) of metals of Group II-A, Group II-B and rare earth metals. For alkylation and dealkylation processes TAPO compositions having pores of at least 5A are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In alkylation of benzene, toluene and xylene, the preferred alkylation agents are olefins such as ethylene and propylene.

The TAPO compositions of this invention may be employed in conventional molecular sieving processes as heretofore have been carried out using aluminosilicate, aluminophosphate or other commonly employed molecular sieves. TAPO compositions are preferably activated prior to their use in a molecular sieve process to remove any molecular species which may be present in the intracrystalline pore system as a result of synthesis or otherwise. For the TAPO compositions this is sometimes accomplished by thermally destroying the organic species present in an as-synthesized TAPO since such organic species may be too large to be desorbed by conventional means.

The TAPO compositions of this invention are also useful as adsorbents and are capable of separating mixtures of molecular species both on the basis of molecular size (kinetic diameters) and based on the degree of polarity of the molecular species. When the separation of molecular species is based upon the selective adsorption based on molecular size, the TAPO is chosen in view of the dimensions of its pores such that at least the smallest molecular species of the mixture can enter the intracrystalline void space while at least the largest specie is excluded. When the separation is based on degree of polarity it is generally the case that the more hydrophilic TAPO will preferentially adsorb the more polar molecular species of a mixture having different degrees of polarity even though both molecular species can communicate with the pore system of the TAPO.

The instant TAPO compositions may be further characterized and distinguished from aluminophosphates by reference to the catalytic properties exhibited by the TAPO compositions. When the TAPO compositions are tested for n-butane cracking and compared with aluminophosphate compositions having a similar topology it has been observed that the TAPO compositions are more active catalysts as indicated by a higher numerical value for n-butane cracking. This comparison will be discussed hereinafter in the examples 38 to 46.

The following examples are provided to exemplify the invention and are not meant to be limiting thereof in any way.

EXAMPLES 1-20

(a) Examples 1 to 20 were carried out to demonstrate the preparation of the TAPO compositions of this invention. The TAPO compositions were carried out by hydrothermal crystallization procedure discussed supra. Reaction mixtures were prepared for each example, unless otherwise noted, using titanium source (titanium isopropoxide; 95 wt percent aqueous solution or titanium acetyl acetonate (75 wt % in isopropanol)), aluminum source (either aluminum isopropoxide or a pseudo-boehmite phase, 75.1% wt. % $Al_2O_3$ and 24.9 wt % $H_2O$), a phosphorus source (85% orthophosphoric acid ($H_3PO_4$)), water and at least one organic template.

The method of addition of the above mentioned components to the reaction mixture was done according to three methods (A, B and C). Methods, A, B and C are as follows:

METHOD A

The water and aluminum isopropoxide were blended to form a homogeneous mixture. Phosphoric acid was added to this mixture and blended to form a homogeneous mixture. The titanium source was added to the above mixture and the mixture blended to form a homogeneous mixture. The organic templating agent (referred to herein as "template") was added to this mixture and blended until a homogeneous mixture was observed.

METHOD B

The water and phosphoric acid were blended to form a homogeneous mixture. The pseudo-boehmite phase was added to this mixture and blended to form a homogeneous mixture. The titanium source was added to this mixture until a homogeneous mixture was observed. The organic template was added to this mixture and blended until a homogeneous mixture was observed.

METHOD C

The water and pseudo-boehmite were blended to form a homogeneous mixture. The titanium source was added to this mixture and blended to for m a homogeneous mixture. Phosphoric acid was added to this mixture and blended to provide a homogeneous mixture after which the organic template was added and the mixture again blended until a homogeneous mixture was observed.

(b) Examples 1 to 20 were carried out by preparing reaction mixtures as above described, using the amounts set forth in Table I.

(c) The composition of the reaction mixtures of Examples 1 to 20 were expressed in terms of the molar ratio of oxides as follows:

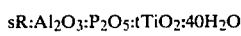

$$sR:Al_2O_3:P_2O_5:tTiO_2:40H_2O$$

wherein "R" is template present in amounts "s" and is the molar ratio of template to mole of $Al_2O_3$, and "t" is the mole ratio of $TiO_2$ to mole of $Al_2O_3$. The selected template and the values for "s" and "t" are set forth in Table II.

(d) The reaction mixtures were then each sealed in a stainless steel pressure vessel lined with polytetrafluoroethylene and heated in an oven at a temperature (see Table II) and for a time (see Table II) at the autogenous pressure. The solid reaction product was recovered by filtration, washed with water and dried at room temperature.

(e) The products obtained in part (d) for Examples 1 to 20 were analyzed by X-ray powder diffraction and characterized to be the TAPO compositions set forth in Table II.

(f) The X-ray patterns carried out herein and all other X-ray patterns appearing herein were obtained using standard X-ray powder diffraction techniques. The radiation source was a high-intensity, copper target, X-ray tube operated at 50 Kv and 40 ma. The diffraction pattern from the copper K radiation and graphite monochromator is suitably recorded by an X-ray spectrometer scintillation counter, pulse height analyzer and strip chart recorder. Flat compressed powder samples are scanned at 20° (2 theta) per minute, using a two second time constant. Interplanar spacings (d) in Angstrom units are obtained from the position of the diffraction peaks expressed as $2\theta$ (theta) where theta is the Bragg angle as observed on the strip chart. Intensities were determined from the heights of diffraction peaks after subtracting background, "$I_o$" being the intensity of the strongest line or peak, and "I" being the intensity of each of the other peaks. When Relative Intensities are reported the following abbreviations mean: vs=very strong; s=strong; m=medium, w=weak; and vw=very weak. Other abbreviations include: sh=shoulder and br=broad.

As will be understood by those skilled in the art the determination of the parameter 2 theta is subject to both human and mechanical error, which in combination, can impose an uncertainty of about ±0.4° on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art.

dard McBain-Bakr gravimetric adsorption apparatus on samples activated in a vacuum at 350° C.

The data for TAPO-5, TAPO-11, TAPO-18 and TAPO-31 were as follows and as set forth in (b), (c), (d) and (e), hereinafter.

(b) TAPO-5:

TABLE I[1]

| Example | Template[2] | Amount[2] | Al-Source[3] | $H_3PO_4$ | Ti-Source[4] | Amount[4] | $H_2O$ | Method |
|---|---|---|---|---|---|---|---|---|
| 1 | TPAOH | 101.5 | 27.2 | 46.2 | TI | 17.9 | 68.5 | B |
| 2 | TPAOH | 203 | 27.2 | 46.2 | TI | 35.9 | 42.7 | B |
| 3 | TPAOH | 101.5 | 27.2 | 46.1 | TI | 71.7 | 65.8 | C |
| 4 | TEAOH | 73.68 | 27.2 | 46.1 | TI | 18.0 | 85.3 | B |
| 5 | TEAOH | 73.68 | 27.2 | 46.1 | TI | 18.0 | 85.3 | B |
| 6 | TEAOH | 73.68 | 27.2 | 46.1 | TI | 18.0 | 85.3 | B |
| 7 | TPAOH | 101.5 | 27.2 | 46.1 | TAC | 58.3 | 69.4 | B |
| 8 | TEAOH | 73.6 | 81.7 | 46.1 | TAC | 58.3 | 92.8 | A |
| 9 | n(Pr)NH | 20.2 | 81.7 | 46.1 | TAC | 29.2 | 137.1 | A |
| 10 | n(Pr)NH | 20.2 | 81.7 | 46.1 | TI | 17.9 | 136.2 | A |
| 11 | n(Pr)NH | 20.2 | 81.7 | 46.1 | TI | 17.9 | 136.2 | A |
| 12 | TEAOH | 147.3 | 27.2 | 46.1 | TAC | 58.3 | 41.8 | B |
| 13 | TEAOH | 147.3 | 27.2 | 46.1 | TAC | 58.3 | 41.8 | B |
| 14 | TEAOH | 147.3 | 81.7 | 46.2 | TI | 17.9 | 47.9 | A |
| 15 | TEAOH | 147.3 | 81.7 | 46.2 | TI | 17.9 | 47.9 | A |
| 16 | TEAOH | 147.3 | 27.2 | 46.1 | TI | 35.9 | 40.0 | B |
| 17 | TMAOH | 36.23 | 27.2 | 46.1 | TI | 17.9 | 111.4 | B |
| 18 | n(Pr)NH | 20.2 | 27.2 | 46.1 | TI | 17.9 | 129.4 | B |
| 19 | n(Pr)NH | 20.2 | 27.2 | 46.1 | TAC | 29.2 | 130.3 | B |
| 20 | TMAOH | 36.23 | 27.2 | 46.1 | TI | 17.9 | 111.4 | B |

[1] all amounts are given in grams
[2] TPAOH = Tetrapropylammonium hydroxide; TEAOH = tetraethylammonium hydroxide; TMAOH = tetramethylammonium hydroxide; and n(Pr)NH = di(n-propyl)amine; amount given in grams.
[3] The aluminum source is identified by reference to the preparative method A, B or C.
[4] The titanium source was titanium isopropoxide (TI) in all examples except examples 7, 8, 9, 12, 13 and 19 wherein the titanium source was titanium acetylacetonate (TAC).

TABLE II

| Example | Template[1] | s | t | Temp (°C.) | Time (hr) | TAPO Product[2] |
|---|---|---|---|---|---|---|
| 1 | TPAOH | 1 | 0.3 | 150 | 264 | TAPO-5 |
| 2 | TPAOH | 2 | 0.6 | 200 | 144 | TAPO-5 |
| 3 | TPAOH | 1 | 1.2 | 150 | 312 | TAPO-5 |
| 4 | TEAOH | 1 | 0.3 | 200 | 144 | TAPO-5; TAPO-18 |
| 5 | TEAOH | 1 | 0.3 | 150 | 216 | TAPO-5; TAPO-18 |
| 6 | TEAOH | 1 | 0.3 | 200 | 216 | TAPO-5; TAPO-18 |
| 7 | TPAOM | 1 | 0.6 | 150 | 120 | TAPO-5 |
| 8 | TEAOH | 1 | 0.6 | 200 | 120 | TAPO-5 |
| 9 | n(Pr)NH | 1 | 0.3 | 150 | 264 | TAPO-11 |
| 10 | n(Pr)NH | 1 | 0.3 | 200 | 120 | TAPO-11 |
| 11 | n(Pr)NH | 1 | 0.3 | 200 | 264 | TAPO-11 |
| 12 | TEAOH | 1 | 0.6 | 150 | 120 | TAPO-18 |
| 13 | TEAOH | 1 | 0.6 | 150 | 264 | TAPO-18 |
| 14 | TEAOH | 2 | 0.3 | 150 | 120 | TAPO-18 |
| 15 | TEAOH | 2 | 0.3 | 150 | 240 | TAPO-18 |
| 16 | TEAOH | 2 | 0.6 | 200 | 144 | TAPO-18 |
| 17 | TMAOH | 1 | 0.3 | 150 | 120 | TAPO-20 |
| 18 | n(Pr)NH | 1 | 0.3 | 200 | 120 | TAPO-31 |
| 19 | n(Pr)NH | 1 | 0.3 | 150 | 120 | TAPO-31; TAPO-11 |
| 20 | TMAOH | 1 | 0.3 | 200 | 264 | TAPO-33 |

[1] TPAOH = tetrapropylammonium hydroxide; TEAOH = tetraethylammonium hydroxide; TMAOH = tetramethylammonium hydroxide; and n(Pr)NH = di(n-propyl)amine
[2] major species as identified by x-ray powder diffraction pattern of product, except that when two species were identified the first species listed was the major species observed.

EXAMPLE 21

(a) The products of examples 8, 10, 13 and 18 were calcined at 600° C., 550° C. and 600° C. and 550° C. in air for 1.5, 1.0, 1.5 and 1.0 hours, respectively. The TAPO's were then employed to determine adsorption capacities of TAPO-5, TAPO-11, TAPO-18 and TAPO-31, respectively, as prepared in these examples. The adsorption capacities were measured using a stan-

| TAPO-5 | | | | |
|---|---|---|---|---|
| | Kinetic Diameter, A° | Pressure (Torr) | Temp. (°C.) | wt % Adsorbed |
| $O_2$ | 3.46 | 101 | −183 | 10.6 |
| $O_2$ | 3.46 | 736 | −183 | 16.1 |
| Cyclohexane | 6.0 | 49 | 22.9 | 10.5 |
| Cyclohexane | 6.0 | 67 | 22.9 | 18.6 |
| $H_2O$ | 2.65 | 11 | 22.4 | 19.1 |
| $H_2O$ | 2.65 | 19 | 22.5 | 28.3 |

(c) TAPO-11:

| TAPO-11 | | | | |
|---|---|---|---|---|
| | Kinetic Diameter, A° | Pressure (Torr) | Temp. (°C.) | wt % Adsorbed |
| $O_2$ | 3.46 | 101 | −183 | 6.7 |
| $O_2$ | 3.46 | 736 | −183 | 9.6 |
| Cyclohexane | 6.0 | 12 | 22.9 | 3.5 |
| Cyclohexane | 6.0 | 67 | 22.9 | 8.5 |
| Neopentane | 6.2 | 101 | Amb* | 1.0** |
| Neopentane | 6.2 | 742 | Amb* | 2.8*** |
| $H_2O$ | 2.65 | 11 | 22.4 | 14.5 |
| $H_2O$ | 2.65 | 19 | 22.5 | 18.7 |

*Amb = ambient temperature
**weight % absorbed after 3 hours
***weight % absorbed after 5.5 hours (d) TAPO-18:

| TAPO-18 | | | | |
|---|---|---|---|---|
| | Kinetic Diameter, A° | Pressure (Torr) | Temp. (°C.) | wt % Adsorbed |
| $O_2$ | 3.46 | 101 | −183 | 24.0 |
| $O_2$ | 3.46 | 739 | −183 | 29.7 |
| n-Hexene | 4.3 | 101 | 24.8 | 19.1 |
| Iso-butane | 5.0 | 103 | 24.5 | 0.68 |
| Iso-butane | 5.0 | 752 | 24.4 | 2.0 |

-continued

TAPO-18

| | Kinetic Diameter, A° | Pressure (Torr) | Temp. (°C.) | wt % Adsorbed |
|---|---|---|---|---|
| H₂O | 2.65 | 11 | 24.4 | 35.7 |
| H₂O | 2.65 | 19 | 24.3 | 38.2 |

(e): TAPO-31:

TAPO-31

| | Kinetic Diameter, A° | Pressure (Torr) | Temp. (°C.) | wt % Adsorbed |
|---|---|---|---|---|
| O₂ | 3.46 | 101 | −183 | 7.2 |
| O₂ | 3.46 | 736 | −183 | 10.4 |
| Cyclohexane | 6.0 | 12 | 22.9 | 4.9 |
| Cyclohexane | 6.0 | 67 | 22.9 | 9.4 |
| Neopentane | 6.2 | 101 | Amb* | 3.9** |
| Neopentane | 6.2 | 742 | Amb* | 7.0*** |
| H₂O | 2.65 | 11 | 22.4 | 13.6 |
| H₂O | 2.65 | 19 | 22.5 | 18.6 |

*Amb = ambient temperature
**weight % adsorbed at 3 hours
***weight % adsorbed at 5.5 hours (f) From the data set forth in parts (b), (c), (d) and (e) it was determined that the pore size of TAPO-5, TAPO-11, TAPO-18 and TAPO-31 were as follows:
(1) TAPO-5: greater than about 6.2A°;
(2) TAPO-11: about 6.0A°;
(3) TAPO-18: about 4.3A°; and
(4) TAPO-31: greater than about 6.2A°

EXAMPLES 22-30

(a) The as-synthesized products of Examples 1, 9, 10, 11, 13, 15, 16, 19 and 20 were analyzed (chemical analysis) to determine the weight percent Al₂O₃, P₂O₅, TiO₂, LOI (Loss on Ignition) and the ratio of carbon to nitrogen present as a result of the template. The results of these analysis are set forth, below, in Table III:

TABLE III

| Example | Sample¹ | Al₂O₃ | P₂O₅ | TiO₂ | LOI | C/N² |
|---|---|---|---|---|---|---|
| 22 | Ex. 1 | 36.7 | 46.4 | 1.3 | 14.2 | 12 |
| 23 | Ex. 9 | 36.3 | 46.7 | 2.7 | 10.8 | 9 |
| 24 | Ex. 10 | 36.3 | 49.5 | 2.0 | 10.6 | 6 |
| 25 | Ex. 11 | 36.7 | 50.0 | 1.2 | 11.9 | 6 |
| 26 | Ex. 13 | 40.5 | 36.9 | 1.38 | 19.1 | 8 |
| 27 | Ex. 15 | 35.3 | 46.2 | 0.23 | 17.5 | 8 |
| 28 | Ex. 16 | 34.9 | 45.3 | 0.57 | 17.9 | 8 |
| 29 | Ex. 19 | 36.9 | 45.3 | 2.5 | 13.3 | 6 |
| 30 | Ex. 20 | 34.1 | 45.0 | 0.18 | 19.4 | 4 |

¹example in which the Sample was prepared
²weight ratio of carbon to nitrogen (b) EDAX (energy dispersive analysis by x-ray) microprobe analysis was carried out on clean crystals (polished with diamond powder and carbon coated) on the product prepared in example 3, supra. The EDAX microprobe analysis showed that 0.6 weight percent titanium was present as an integral part of the crystal particle of the TAPO composition. The relative amounts of P₂O₅, Al₂O₃, and TiO₂, normalized to 100 percent based on P₂O₅, Al₂O₃ and TiO₂ and expressed as a weight percent was P₂O₅ 58.7; Al₂O₃ 40.6; TiO₂ 0.67.

EDAX microprobe analysis was carried out on the products of examples 10 and 15 but the results were inconclusive owing to the small size of the crystals employed for analysis and possibly the amount of titanium present.

(c) EDAX (energy dispersive analysis by-x-ray) microprobe analysis was carried out on TAPO crystals prepared in examples 1 and 10, supra. The EDAX microprobe analysis is set forth in the following table. With relative amounts of TiO₂, normalized to 100 percent based on P₂O₅, Al₂O₃ and TiO₂ and expressed as a weight percent being as follows:

| TAPO | Example | TiO₂ |
|---|---|---|
| TAPO-5 | 1 | ~2 |
| TAPO-11 | 10 | ~1 to 2 |

Several other TAPO compositions were analyzed by the use of EDAX but these analyses were not definitive due to the crystal size requirement and/or detection limits of EDAX.

EXAMPLE 31

(a) TAPO-5, as referred to in example 8, was subjected to x-ray analysis. TAPO-5 was determined to have a characteristic x-ray powder diffraction pattern which contains at least the d-spacing set forth in Table V below:

TABLE V

| 2θ | d, (A) | Relative Intensity |
|---|---|---|
| 7.5 | 11.78 | vs |
| 15.0 | 5.91 | m |
| 19.9 | 4.46 | m |
| 21.0 | 4.23 | m |
| 22.5 | 3.95 | s |
| 26.2 | 3.401 | m |

The as-synthesized TAPO-5 compositions for which x-ray powder diffraction data have been obtained, include in the TAPO characterized by Table V, to date have patterns which are characterized by the data of Table VI below:

TABLE VI

| 2θ | d, (A) | 100 × I/I₀ |
|---|---|---|
| 7.5 | 11.78 | 100 |
| 9.7* | 9.12 | 2 |
| 13.0 | 6.81 | 11 |
| 15.0 | 5.91 | 25 |
| 19.9 | 4.46 | 45 |
| 21.0 | 4.23 | 56 |
| 21.8 (sh)* | 4.08 | — |
| 22.5 | 3.95 | 89 |
| 24.8 | 3.59 | 12 |
| 25.4 (sh)* | 3.507 | — |
| 26.2 | 3.401 | 32 |
| 29.0 | 3.079 | 18 |
| 30.2 | 2.959 | 19 |
| 33.7 | 2.660 | 6 |
| 34.8 | 2.578 | 16 |
| 37.2 | 2.417 | 5 |
| 37.8 | 2.380 | 14 |
| 41.8 | 2.161 | 3 |
| 42.6 | 2.122 | 3 |
| 48.0 | 1.895 | 8 | sh = shoulder
*peak may contain an impurity (b) A portion of the as-synthesized TAPO-5 of part (a) was calcined in air at 600° C. for about 1.5 hours. The calcined product was characterized by the x-ray powder diffraction pattern of Table A, below:

TABLE A

| 2θ | d, (A) | Relative Intensity |
|---|---|---|
| 7.4 | 11.95 | vs |

TABLE A-continued

| 2θ | d, (A) | Relative Intensity |
|---|---|---|
| 12.9 | 6.86 | w |
| 19.7 | 4.51 | m |
| 21.2 | 4.19 | m |
| 22.4 | 3.97 | s |
| 25.9 | 3.440 | m |

The calcined TAPO-5 compositions for which x-ray powder diffraction data have been obtained to date have patterns which are characterized by the x-ray powder diffraction pattern shown in Table B, below:

TABLE B

| 2θ | d, (A) | 100 × I/I$_o$ |
|---|---|---|
| 7.4 | 11.95 | 100 |
| 12.9 | 6.86 | 17 |
| 14.9 | 5.95 | 7 |
| 19.7 | 4.51 | 27 |
| 21.2 | 4.19 | 39 |
| 21.8* | 4.08 | 8 |
| 22.4 | 3.97 | 70 |
| 24.9 | 3.58 | 9 |
| 25.9 | 3.440 | 25 |
| 29.0 | 3.079 | 13 |
| 30.0 | 2.978 | 13 |
| 33.7 | 2.660 | 4 |
| 34.5 | 2.600 | 9 |
| 37.0 | 2.430 | 4 |
| 37.8 | 2.380 | 10 |
| 42.3 | 2.137 | 2 |
| 43.1 | 2.099 | 2 |
| 47.7 | 1.907 | 4 |

*peak may contain an impurity

EXAMPLE 32

(a) TAPO-11, as referred to in example 10, was subjected to x-ray analysis. TAPO-11 was determined to have a characteristic x-ray powder diffraction pattern which contains at least the d-spacings set forth in Table VII, below:

TABLE VII

| 2θ | d, (A) | Relative Intensity |
|---|---|---|
| 9.5 | 9.31 | m |
| 20.5 | 4.33 | m |
| 20.9 | 4.25 | vs |
| 22.2 | 4.00 | s |
| 22.6 | 3.93 | s |
| 23.2 | 3.83 | s |

All of the as-synthesized TAPO-11 compositions for which x-ray powder diffraction data have been obtained to date have patterns which are characterized by the data of Table VIII, below:

TABLE VIII

| 2θ | d, (A) | 100 × I/I$_o$ |
|---|---|---|
| 8.1 | 10.92 | 35 |
| 9.5 | 9.31 | 55 |
| 13.2 | 6.71 | 17 |
| 15.7 | 5.64 | 32 |
| 16.3 | 5.44 | 5 |
| 19.0 | 4.67 | 7 |
| 20.5 | 4.33 | 52 |
| 20.9 | 4.25 | 100 |
| 22.2 | 4.00 | 67 |
| 22.6 | 3.93 | 73 |
| 23.2 | 3.83 | 74 |
| 24.8 | 3.59 | 15 |
| 26.4 | 3.376 | 17 |
| 26.6 | 3.351 | 19 |
| 28.4 | 3.143 | — |
| 28.7 | 3.110 | 18 |
| 29.1 | 3.069 | 8 |
| 29.5 | 2.028 | 10 |
| 31.5 | 2.840 | 12 |
| 33.0 | 2.714 | 19 |
| 34.3 | 2.614 | 11 |
| 35.7 | 2.515 | 6 |
| 36.6 | 2.456 | 7 |
| 37.6 | 2.392 | 15 |
| 37.8 | 2.380 | 16 |
| 39.3 | 2.292 | 4 |
| 42.2 | 2.141 | 4 |
| 42.8 | 2.113 | 5 |
| 45.0 | 2.014 | 6 |
| 46.0 | 1.973 | 3 |
| 47.1 | 1.929 | 3 |
| 48.1 | 1.892 | 3 |
| 48.9 | 1.863 | 5 |
| 50.8 | 1.797 | 6 |
| 54.8 | 1.675 | 6 |

(b) A portion of the as-synthesized TAPO-11 of part (a) was calcined in air at 550° C. for 1.5 hours. The calcined product was characterized by the x-ray powder diffraction pattern of Table C, below:

TABLE C

| 2θ | d, (A) | 100 × I/I$_o$ |
|---|---|---|
| 9.8 | 9.03 | m |
| 16.1 | 5.51 | m |
| 21.9 | 4.06 | vs |
| 22.4 | 3.97 | m |
| 23.5 | 3.79 | m |
| 29.7 | 3.008 | m |

All of the calcined TAPO-11 compositions for which x-ray powder diffraction data have been obtained to date have patterns which are characterized by the data of Table D, below:

TABLE D

| 2θ | d, (A) | 100 × I/I$_o$ |
|---|---|---|
| 8.1 | 10.92 | 22 |
| 9.8 | 9.03 | 42 |
| 11.7 | 7.56 | 7 |
| 12.8 | 6.92 | 22 |
| 13.7 | 6.46 | 9 |
| 14.6 | 6.07 | 6 |
| 16.1 | 5.51 | 54 |
| 17.5 | 5.07 | 6 |
| 19.5 (sh) | 4.55 | 19 |
| 19.9 | 4.46 | 25 |
| 20.8 | 4.27 | 12 |
| 21.9 | 4.06 | 100 |
| 22.4 (sh) | 3.97 | 54 |
| 23.5 | 3.79 | 57 |
| 24.0 | 3.71 | 20 |
| 24.3 (sh) | 3.66 | 17 |
| 25.8 | 3.453 | 24 |
| 26.7 | 3.339 | 16 |
| 27.2 | 3.278 | 18 |
| 27.8 | 3.209 | 22 |
| 28.6 | 3.121 | 10 |
| 29.7 | 3.008 | 32 |
| 30.4 | 2.940 | 19 |
| 31.8 | 2.814 | 12 |
| 32.6 | 2.755 | 22 |
| 34.0 | 2.637 | 12 |
| 34.5 | 2.600 | 7 |
| 35.6 | 2.522 | 14 |
| 37.2 | 2.417 | 11 |
| 38.2 (sh) | 2.356 | 6 |
| 38.6 | 2.332 | 16 |
| 41.0 | 2.201 | 10 |
| 43.6 | 2.076 | 4 |
| 44.6 | 2.032 | 8 |
| 45.2 | 2.006 | 4 |

TABLE D-continued

| 2θ | d, (A) | 100 × I/I$_o$ |
|---|---|---|
| 49.1 | 1.855 | 11 |
| 49.6 | 1.838 | 10 |
| 50.4 | 1.811 | 4 |
| 52.4 | 1.746 | 4 |
| 53.7 | 1.707 | 5 |
| 54.7 | 1.678 | 4 |

EXAMPLE 33

(a) TAPO-18, as referred to in example 15, was subjected to x-ray analysis. TAPO-18 was determined to have a characteristic x-ray powder diffraction pattern which contains at least the d-spacings set forth in Table IX below:

TABLE IX

| 2θ | d, (A) | Relative Intensity |
|---|---|---|
| 9.643 | 9.17 | vs |
| 16.879 | 5.25 | m |
| 17.061 | 5.20 | m |
| 22.227 | 4.00 | m |
| 25.354 | 3.513 | m |
| 25.462 | 3.498 | m |
| 26.685 | 3.341 | s |

(b) All of the as-synthesized TAPO-18 compositions for which X-ray powder diffraction data have been obtained to date have patterns which are characterized by the data of Table X, below:

TABLE X

| 2θ | d, (A) | 100 × I/I$_o$ |
|---|---|---|
| 9.643 | 9.17 | 100 |
| 10.474 | 8.45 | 3 |
| 11.035 | 8.02 | 5 |
| 13.193 | 6.71 | 2 |
| 14.055 | 6.30 | 3 |
| 14.834 | 5.97 | 3 |
| 15.554 | 5.70 | 12 |
| 16.879 | 5.25 | 28 |
| 17.061 | 5.20 | 29 |
| 17.943 | 4.94 | 20 |
| 18.957* | 4.68 | 12 |
| 19.3 | 4.6 | 1 |
| 19.556 | 4.53 | 2 |
| 20.210 | 4.39 | 20 |
| 20.729 | 4.29 | 3 |
| 21.040 | 4.22 | 22 |
| 22.227 | 4.00 | 27 |
| 23.404 | 3.80 | 3 |
| 23.978 | 3.71 | 4 |
| 24.478 | 3.64 | 7 |
| 24.6 (sh) | 3.62 | — |
| 25.001 | 3.562 | 11 |
| 25.354* | 3.513 | 34 |
| 25.462 | 3.498 | 32 |
| 26.173 | 3.401 | 6 |
| 26.685 | 3.340 | 60 |
| 27.4 | 3.260 | 1 |
| 28.149 | 3.170 | 15 |
| 29.327 | 3.045 | 6 |
| 30.135 | 2.966 | 13 |
| 30.877 | 2.896 | 5 |
| 31.428 | 2.846 | 9 |
| 31.899 | 2.805 | 2 |
| 32.525 | 2.753 | 17 |
| 33.542 | 2.672 | 3 |
| 34.451 | 2.603 | 2 |
| 34.547* | 2.596 | 2 |
| 36.100 | 2.488 | 8 |
| 37.833 | 2.378 | 3 |
| 38.051 | 2.365 | 2 |
| 38.356 | 2.347 | 2 |
| 38.501 | 2.338 | 2 |
| 39.9 | 2.26 | 1 |

TABLE X-continued

| 2θ | d, (A) | 100 × I/I$_o$ |
|---|---|---|
| 41.890 | 2.157 | 3 |
| 43.123 | 2.098 | 3 |
| 43.6 | 2.080 | 1 |
| 45.342* | 2.000 | 6 |
| 46.795* | 1.941 | 8 |
| 47.372* | 1.919 | 4 |
| 47.887 | 1.899 | 6 |
| 48.731* | 1.867 | 15 |
| 49.675 | 1.835 | 6 |
| 50.058 | 1.822 | 2 |
| 51.159 | 1.785 | 2 |
| 52.114 | 1.755 | 2 |
| 54.081 | 1.696 | 2 |
| 54.249 | 1.691 | 2 |
| 54.671 | 1.678 | 3 |
| 55.260 | 1.662 | 3 |

*peak may contain an impurity
sh = shoulder

EXAMPLE 34

(a) TAPO-18, as referred to in example 15, was subjected to X-ray analysis after calcination at 550° C. in air for 1 hour. TAPO-18 was determined to have a characteristic X-ray powder diffraction pattern which contains at least the d-spacing set forth in Table E, below:

TABLE E

| 2θ | d, (A) | Relative Intensity |
|---|---|---|
| 9.5 | 9.31 | vs |
| 9.6 | 9.21 | vs |
| 21.8 | 4.08 | m |
| 22.9 | 3.88 | w |
| 29.0 | 3.079 | m |
| 31.0 | 2.885 | m |

(b) All of the calcined TAPO-18 compositions for which X-ray powder diffraction data have been obtained to date have patterns which are characterized by the data of Table F, below:

TABLE F

| 2θ | d, (A) | 100 × I/I$_o$ |
|---|---|---|
| 9.5 | 9.31 | 97 |
| 9.6 | 9.21 | 100 |
| 10.6 | 8.35 | 10 |
| 11.2 | 7.90 | 10 |
| 13.4 | 6.61 | 18 |
| 14.4 | 6.15 | 10 |
| 16.0 | 5.54 | 13 |
| 16.5 | 5.37 | 5 |
| 17.1 | 5.19 | 18 |
| 17.5 | 5.07 | 15 |
| 18.4 | 4.82 | 6 |
| 19.0 | 4.67 | 7 |
| 19.5 | 4.55 | 3 |
| 20.7 | 4.29 | 13 |
| 21.8 | 4.08 | 46 |
| 22.9 | 3.88 | 15 |
| 24.2 | 3.68 | 11 |
| 24.7 | 3.60 | 10 |
| 25.5 | 3.493 | 8 |
| 26.2 | 3.401 | 7 |
| 27.1 | 3.290 | 18 |
| 27.5 (sh) | 3.243 | — |
| 28.2 | 3.164 | 5 |
| 29.0 | 3.079 | 21 |
| 29.4 | 3.038 | 10 |
| 29.8 | 2.998 | 10 |
| 31.0 | 2.885 | 23 |
| 31.5 | 2.840 | 12 |
| 31.9 | 2.805 | 7 |
| 32.4 | 2.763 | 6 |
| 33.1 | 2.706 | 8 |

TABLE F-continued

| 2θ | d, (A) | 100 × I/I₀ |
|---|---|---|
| 33.7 | 2.660 | 11 |
| 34.6 | 2.592 | 5 |
| 35.5 | 2.529 | 6 |
| 36.9 | 2.436 | 6 |
| 38.9 | 2.315 | 5 |
| 42.7 | 2.118 | 4 |
| 44.7 | 2.027 | 3 |
| 46.8 | 1.941 | 2 |
| 47.8 | 1.903 | 4 |
| 49.3 | 1.848 | 2 |
| 49.7 | 1.834 | 3 |
| 51.8 | 1.765 | 4 |
| 54.0 | 1.698 | 3 |

EXAMPLE 35

(a) TAPO-20, as referred to in example 17, was subjected to X-ray analysis. TAPO-20 was determined to have a characteristic X-ray powder diffraction pattern which contains at least the d-spacings set forth in Table XI, below:

TABLE XI

| 2θ | d, (A) | Relative Intensity |
|---|---|---|
| 14.0 | 6.33 | m |
| 19.8 | 4.48 | m |
| 24.4 | 3.65 | vs |
| 28.2 | 3.164 | m |
| 31.6 | 2.831 | w |
| 34.6 | 2.592 | w |

All of the as-synthesized TAPO-20 compositions for which X-ray powder diffraction data have been obtained to date have patterns which are characterized by the data of Table XII, below:

TABLE XII

| 2θ | d, (A) | 100 × I/I₀ |
|---|---|---|
| 14.0 | 6.33 | 52 |
| 19.8 | 4.48 | 46 |
| 21.3* | 4.17 | 2 |
| 21.9* | 4.06 | 4 |
| 22.3 | 3.99 | 10 |
| 22.5 (sh) | 3.95 | — |
| 23.0* | 3.87 | 2 |
| 24.4* | 3.65 | 100 |
| 28.2 | 3.164 | 21 |
| 31.6 | 2.831 | 12 |
| 34.6 | 2.592 | 17 |
| 37.6 | 2.392 | — |
| 38.4* | 2.344 | 2 |
| 40.2 | 2.243 | 1 |
| 42.9 | 2.108 | 5 |
| 47.8 | 1.903 | 2 |
| 52.2 | 1.752 | 12 | sh = shoulder
*peak may contain an impurity (b) A portion of the as-synthesized TAPO-20 of part (a) was calcined in air at 550° C. for 1.0 hour. The calcined product was characterized by the X-ray powder diffraction pattern contain at least the d-spacing of Table G, below:

TABLE G

| 2θ | d, (A) | Relative Intensity |
|---|---|---|
| 14.3 | 6.19 | vs |
| 20.2 | 4.40 | w |
| 24.6 | 3.62 | m |
| 28.5 | 3.132 | w |
| 31.8 | 2.814 | vm |

TABLE G-continued

| 2θ | d, (A) | Relative Intensity |
|---|---|---|
| 35.0 | 2.564 | w |

All the calcined TAPO-20 compositions for which X-ray powder diffraction data have been obtained to date have patterns which are characterized by the X-ray powder diffraction pattern of Table H, below:

TABLE H

| 2θ | d, (A) | 100 × I/I₀ |
|---|---|---|
| 14.3 | 6.19 | 100 |
| 20.2 | 4.40 | 15 |
| 22.5 | 3.95 | 5 |
| 24.6 | 3.62 | 48 |
| 28.5 | 3.132 | 11 |
| 31.8 | 2.814 | 9 |
| 35.0 | 2.564 | 10 |
| 37.9 | 2.374 | 1 |
| 40.7 | 2.217 | 2 |
| 43.2 | 2.100 | 2 |
| 48.2 | 1.888 | 2 |
| 52.6 | 1.740 | 6 |

EXAMPLE 36

(a) TAPO-31, as referred to in example 18, was subjected to X-ray analysis. TAPO-31 was determined to have a characteristic X-ray powder diffraction pattern which contains at least the d-spacings set forth in Table XIII, below:

TABLE XIII

| 2θ | d, (A) | Relative Intensity |
|---|---|---|
| 8.5 | 10.40 | m |
| 20.9 | 4.25 | s |
| 21.2 | 4.19 | s |
| 22.5 | 3.95 | vs |
| 22.7 | 3.92 | vs |

All of the as-synthesized TAPO-31 compositions for which X-ray powder diffraction data have been obtained to data have patterns which are characterized by the date of Table XIV, below:

TABLE XIV

| 2θ | d, (A) | 100 × I/I₀ |
|---|---|---|
| 7.0 | 12.63 | 21 |
| 8.5 | 10.40 | 56 |
| 9.6 | 9.21 | 20 |
| 9.8 (sh) | 9.03 | — |
| 11.8* | 7.50 | 10 |
| 13.3 | 6.66 | 9 |
| 13.8 | 6.42 | 13 |
| 14.8 | 5.99 | 4 |
| 15.8 | 5.61 | 7 |
| 17.0 | 5.22 | 4 |
| 18.4 | 4.82 | 8 |
| 19.1 | 4.65 | 5 |
| 20.2 (sh) | 4.40 | — |
| 20.4 | 4.35 | 48 |
| 20.9* | 4.25 | 60 |
| 21.2 | 4.19 | 68 |
| 22.0 | 4.04 | 43 |
| 22.5* | 3.95 | 94 |
| 22.7 | 3.92 | 100 |
| 23.3 (sh) | 3.82 | 35 |
| 24.6 (sh) | 3.62 | — |
| 25.4 | 3.507 | 16 |
| 26.3 (sh)* | 3.389 | — |
| 26.5* | 3.363 | 50 |
| 26.7 (sh)* | 3.339 | — |
| 27.8 | 3.209 | 13 |
| 28.2 | 3.164 | — |

TABLE XIV-continued

| 2θ | d, (A) | 100 × I/I₀ |
|---|---|---|
| 28.8* | 3.100 | 8 |
| 29.6 | 3.018 | 16 |
| 30.0 | 2.979 | 5 |
| 31.5* | 2.840 | 14 |
| 33.0 | 2.714 | 5 |
| 33.6 | 2.667 | 5 |
| 35.1 | 2.557 | 7 |
| 35.9 | 2.501 | 8 |
| 37.8 | 2.380 | 13 |
| 40.0 | 2.254 | 7 |
| 42.2 | 2.141 | 16 |
| 49.7 | 1.834 | 12 | sh = shoulder
*peak may contain an impurity (b) A portion of the as-synthesized TAPO-31 of part (a) was calcined in air at 550° C. for 1.0 hours. The calcined product was characterized by the X-ray powder diffraction pattern of Table M, below:

TABLE M

| 2θ | d, (A) | Relative Intensity |
|---|---|---|
| 8.5 | 10.40 | vs |
| 9.8 | 9.03 | w |
| 20.3 | 4.37 | m |
| 22.1 | 4.02 | s |
| 22.6 | 3.93 | vs |
| 31.7 | 2.823 | m |

All the calcined TAPO-31 compositions for which X-ray powder diffraction data have been obtained to date have pattern which are characterized by the data of Table N, below:

TABLE N

| 2θ | d, (A) | 100 × I/I₀ |
|---|---|---|
| 5.8* | 15.24 | 3 |
| 6.6* | 13.39 | 4 |
| 8.5 | 10.40 | 100 |
| 9.8 | 9.03 | 17 |
| 12.8* | 6.92 | 6 |
| 13.5 | 6.56 | 9 |
| 14.8 | 5.99 | 8 |
| 16.2 | 5.47 | 9 |
| 17.0 | 5.22 | 11 |
| 18.4 | 4.82 | 6 |
| 20.3 | 4.37 | 50 |
| 21.7 (sh) | 4.10 | — |
| 22.1 | 4.02 | 60 |
| 22.6 | 3.93 | 96 |
| 23.0 (sh) | 3.87 | — |
| 23.5 | 3.79 | 16 |
| 25.2 | 3.534 | 14 |
| 25.7 | 3.466 | 16 |
| 28.0 | 3.187 | 16 |
| 29.7 | 3.008 | 17 |
| 30.3 | 2.950 | 6 |
| 30.9 | 2.894 | 6 |
| 31.7 | 2.823 | 27 |
| 32.5* | 2.765 | 6 |
| 35.1 | 2.556 | 12 |
| 36.2 | 2.481 | 5 |
| 37.2 | 2.417 | 6 |
| 38.2 | 2.356 | 6 |
| 39.4 | 2.287 | 6 |
| 40.2 | 2.243 | 6 |
| 44.0 | 2.058 | 4 |
| 45.0 | 2.014 | 4 |
| 46.6 | 1.950 | 5 |
| 47.6 | 1.910 | 4 |
| 48.6 | 1.873 | 5 |
| 49.1 | 1.855 | 4 |
| 50.9 | 1.794 | 4 |

TABLE N-continued

| 2θ | d, (A) | 100 × I/I₀ |
|---|---|---|
| 51.6 | 1.771 | 6 | sh = shoulder
*peak may contain an impurity

EXAMPLE 37

(a) TAPO-33, as referred to in example 20, was subjected to X-ray analysis. TAPO-33 was determined to have a characteristic X-ray powder diffraction pattern which contains at least the d-spacings set forth in Table XV, below:

TABLE XV

| 2θ | d, (A) | Relative Intensity |
|---|---|---|
| 9.3 | 9.51 | m |
| 12.6 | 7.03 | vs |
| 20.5 | 4.33 | m |
| 23.9 | 3.72 | m |
| 26.1 | 3.414 | m |
| 27.4 | 3.255 | s |

All of the as-synthesized TAPO-33 compositions for which X-ray powder diffraction data have been obtained to date have patterns which are characterized by the data of Table XVI, below:

TABLE XVI

| 2θ | d, (A) | 100 × I/I₀ |
|---|---|---|
| 9.3 | 9.51 | 24 |
| 12.6 | 7.03 | 100 |
| 13.9* | 6.37 | 3 |
| 15.3 | 5.79 | 14 |
| 17.0 | 5.22 | 13 |
| 17.5 | 5.07 | 14 |
| 18.0 | 4.93 | 1 |
| 19.4 | 4.58 | 3 |
| 19.8 (sh)* | 4.48 | — |
| 20.5 | 4.33 | 22 |
| 20.9 | 4.25 | 3 |
| 22.2 | 4.00 | 3 |
| 23.0 | 3.87 | 5 |
| 23.9 | 3.72 | 26 |
| 24.3 | 3.66 | 5 |
| 25.0 | 3.562 | 4 |
| 26.1 | 3.414 | 28 |
| 27.4 | 3.255 | 77 |
| 28.2 (sh) | 3.164 | — |
| 29.5 | 3.028 | 13 |
| 30.7 | 2.912 | 6 |
| 31.4 | 2.848 | 1 |
| 32.0 | 2.797 | 8 |
| 32.6 | 2.747 | 1 |
| 34.3 | 2.614 | 8 |
| 35.4 | 2.543 | 2 |
| 36.8 | 2.442 | 2 |
| 37.8 | 2.380 | 3 |
| 39.0 | 2.309 | 2 |
| 39.4 | 2.286 | 1 |
| 40.3 | 2.238 | 2 |
| 41.5 | 2.176 | 2 |
| 45.2 | 2.006 | 2 |
| 46.8 | 1.941 | 4 |
| 47.8 | 1.903 | 7 |
| 49.4 | 1.845 | 2 |
| 49.8 | 1.831 | 2 |
| 52.0 | 1.758 | 6 |
| 52.8 | 1.734 | 6 |
| 54.0 | 1.698 | 2 |
| 54.4 | 1.687 | 3 |
| 55.2 | 1.664 | 4 | sh = shoulder
*peak may contain an impurity (b) A portion of the as-synthesized TAPO-33 of part (a) was calcined in air at 550° C. for 1 hour. The calcined product was characterized by the X-ray powder diffraction pattern of Table O, below:

TABLE O

| 2θ   | d, (A) | Relative Intensity |
|------|--------|--------------------|
| 9.5  | 9.31   | m                  |
| 13.2 | 6.71   | vs                 |
| 18.1 | 4.90   | m                  |
| 21.2 | 4.19   | s                  |
| 26.7 | 3.339  | m                  |
| 32.0 | 2.797  | m                  |

All of the calcined TAPO-33 compositions for which X-ray powder diffraction data have been obtained to date have patterns which are characterized by the date of Table P, below:

TABLE P

| 2θ       | d, (A) | 100 × I/I$_o$ |
|----------|--------|---------------|
| 9.5      | 9.31   | 47            |
| 13.2     | 6.71   | 100           |
| 14.1     | 6.28   | 11            |
| 14.6     | 6.07   | 11            |
| 15.0*    | 5.91   | 23            |
| 15.8     | 5.61   | 16            |
| 18.1     | 4.90   | 44            |
| 18.4     | 4.82   | 31            |
| 18.9*    | 4.70   | 27            |
| 20.1     | 4.42   | 24            |
| 21.2     | 4.19   | 63            |
| 22.5     | 3.95   | 18            |
| 24.2     | 3.68   | 19            |
| 24.6     | 3.62   | 24            |
| 25.3 (sh)| 3.520  | —             |
| 25.4     | 3.507  | 16            |
| 25.9     | 3.440  | 13            |
| 26.7     | 3.339  | 41            |
| 27.0     | 3.302  | 24            |
| 28.4 (sh)| 3.143  | —             |
| 28.9     | 3.089  | 24            |
| 29.3     | 3.048  | 17            |
| 30.2     | 2.959  | 29            |
| 30.9*    | 2.894  | 14            |
| 31.5 (sh)| 2.840  | 12            |
| 32.0     | 2.797  | 44            |
| 33.0     | 2.714  | 10            |
| 33.9     | 2.644  | 10            |
| 34.4     | 2.607  | 7             |
| 36.9     | 2.436  | 7             |
| 37.3     | 2.411  | 8             |
| 38.2     | 2.356  | 10            |
| 38.6     | 2.332  | 8             |
| 39.1     | 2.303  | 7             |
| 39.9     | 2.259  | 5             |
| 40.8     | 2.211  | 6             |
| 42.3     | 2.137  | —             |
| 44.3     | 2.050  | 6             |
| 47.8     | 1.900  | 9             | sh = shoulder
*peak may contain an impurity

EXAMPLES 38 TO 46

In order to demonstrate the catalytic activity of the TAPO compositions, calcined samples of the products of Examples 1, 11, 12, 14, 18 and 20 were then tested for catalytic cracking. Further, comparative examples were carried out to provide compositions witht AlPO$_4$-5 (example 44), amorphous TiO$_2$ and 95 wt % AlPO$_4$-18 (example 46). The AlPO$_4$-5 and AlPO$_4$-18 were prepared as described in examples 1-26 and 46 of U.S. Pat. No. 4,310,440. The amorphous TiO$_2$ (example 45) was prepared using 17.9 grams of titanium isopropoxide which was hydrolyzed using 45.5 grams of water and 23.0 grams of phosphoric acid and then filtering and washing the product. The test procedure employed was the catalytic cracking of premixed two (2) mole % n-butane in helium stream in a ½" O.D. quartz tube reactor over up to about 5 grams (20-40 mesh) of the particular TAPO sample to be tested. The sample was activated in situ for 60 minutes at 500° C. under 200 cm$^3$/min dry helium purge. Then the two (2) mole (percent) n-butane in helium at a flow rate of 50 cm$^3$/min was passed over the sample for 40 minutes with product stream analysis being carried out at 10 minute intervals. The pseudo-first-order rate constant (k$_a$) was then calculated to determine the catalytic activity of the TAPO composition. The k$_a$ value (cm$^3$/g min) obtained for the TAPO compositions are set forth, below, in Table XVII.

TABLE XVII

| Example | Sample      | Rate Constant (k$_a$) |
|---------|-------------|-----------------------|
| 38      | Ex. 1       | 0.17                  |
| 39      | Ex. 11      | 0.12                  |
| 40      | Ex. 12      | 0.07                  |
| 41      | Ex. 14      | 0.25                  |
| 42      | Ex. 18      | 0.1                   |
| 43      | Ex. 20      | 0.2                   |
| 44      | Comparative | 0.05                  |
| 45      | Comparative | 0.4                   |
| 46      | Comparative | 0.08                  |

What is claimed is:

1. Process for converting a hydrocarbon which comprises contacting said hydrocarbon under effective process conditions, wherein the process is a cracking process with at least one crystalline molecular sieve selected from the group consisting of crystalline molecular sieves comprising pores having nominal diameters of greater than about 3 Angstroms and whose chemical composition in the as-synthesized and anhydrous form is represented by the unit empirical formula:

$$mR:(Ti_xAl_yP_z)O_2$$

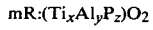

wherein "R" represents at least one organic templating agent present in the intracrystalline pore system; "m" represents the moles of "R" present per mole of (Ti$_x$Al$_y$P$_z$)O$_2$ has a value of between zero and about 5.0; and "x", "y" and "z" represent the mole fractions of titanium, aluminum and phosphorus, respectively, present as tetrahederal oxides, said mole fractions being such that they are within the pentagonal compositional area defined by points A, B, C, D and E of the ternary diagram which is FIG. 1 of the drawings and points A, B, C, D and E representing the following values for "x", "y" and "z":

|       | Mole Fraction |      |       |
|-------|---------------|------|-------|
| Point | x             | y    | z     |
| A     | 0.001         | 0.45 | 0.549 |
| B     | 0.88          | 0.01 | 0.01  |
| C     | 0.98          | 0.01 | 0.01  |
| D     | 0.29          | 0.70 | 0.01  |
| E     | 0.001         | 0.70 | 0.299 |

2. The process of claim 1 wherein the crystalline molecular sieves have mole fractions of titanium, aluminum and phosphorus which are within the pentagonal compositional area defined by points a, b, c, d and e of the ternary diagram which is FIG. 2 of the drawings wherein a, b, c, d and e have the following values:

|       | Mole Fraction |       |       |
| Point | x     | y     | z     |
| ----- | ----- | ----- | ----- |
| a     | 0.002 | 0.499 | 0.499 |
| b     | 0.20  | 0.4   | 0.40  |
| c     | 0.20  | 0.5   | 0.30  |
| d     | 0.10  | 0.6   | 0.30  |
| e     | 0.002 | 0.6   | 0.398 |

3. The process of claim 1 wherein the molecular sieves have been calcined.

4. The process of claim 2 wherein the molecular sieves have been calcined.

5. Process for converting a hydrocarbon which comprises contacting said hydrocarbons under effective process conditions wherein the process is a cracking process with at least one crystalline molecular sieve selected from the group consisting of crystalline molecular sieves comprising a composition expressed in terms of mole ratios of oxides in the anhydrous form as $$vR:pTiO_2:qAl_2O_3:rP_2O_5$$

wherein "R" represents at least one organic templating agent; "v" represents an effective amount of organic templating agent; "p", "q" and "r" represent moles, respectively, of $TiO_2$, $Al_2O_3$ and $P_2O_5$, based on said moles being such that they are within the pentagonal compositional area defined by points A, B, C, D and E of the ternary diagram which is FIG. 1 of the drawings said points A, B, C, D and E representing the following values for "p", "q" and "r":

|       | Moles |     |        |
| Point | p     | q   | r      |
| ----- | ----- | --- | ------ |
| A     | 0.004 | 1.0 | 1.22   |
| B     | 176   | 1.0 | 11.0   |
| C     | 196   | 1.0 | 1.0    |
| D     | 0.828 | 1.0 | 0.0143 |
| E     | 0.003 | 1.0 | 0.427  |

6. The process of claim 5 wherein the molecular sieves have mole fractions of $TiO_2$, $Al_2O_3$ and $P_2O_5$ within the pentagonal compositional area defined by points a, b, c, d and e of the ternary diagram which is FIG. 2 of the drawings wherein a, b, c, d and e have the following values:

|       | Moles |     |       |
| Point | p     | q   | r     |
| ----- | ----- | --- | ----- |
| a     | 0.008 | 1.0 | 1.0   |
| b     | 1.0   | 1.0 | 1.0   |
| c     | 0.80  | 1.0 | 0.65  |
| d     | 0.333 | 1.0 | 0.50  |
| e     | 0.67  | 1.0 | 0.663 |

7. The process of claim 5 wherein "v" has a value between zero and about 3.0.

8. The process of claim 3 or claim 4 wherein crystalline molecular sieves have the characteristic x-ray powder diffraction pattern set forth in any one of Tables A, C, E, G, M or O.

9. The process of claim 3 or claim 4 wherein such crystalline molecular sieves are calcined in air at a temperature between about 200° C. and about 700° C. for a period of time sufficient to remove at least a portion of template R.

10. Process for converting a hydrocarbon which comprises contacting said hydrocarbon under effective process conditions wherein the process is a hydrocracking process with at least one crystalline molecular sieve selected from the group consisting of crystalline molecular sieves comprising pores having nominal diameters of greater than about 3 Angstroms and whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of $(Ti_xAl_yP_z)O_2$ has a value of between zero and about 5.0; and "x", "y" and "z" represent the mole fractions of titanium, aluminum and phosphorus, respectively, present as tetrahederal oxides, said mole fractions being such that they are within the pentagonal compositional area defined by points A, B, C, D and E of the ternary diagram which is FIG. 1 of the drawings and points A, B, C, D and E representing the following values for "x", "y" and "z":

|       | Mole Fraction |      |       |
| Point | x     | y     | z     |
| ----- | ----- | ----- | ----- |
| A     | 0.001 | 0.45  | 0.549 |
| B     | 0.88  | 0.01  | 0.01  |
| C     | 0.98  | 0.01  | 0.01  |
| D     | 0.29  | 0.70  | 0.01  |
| E     | 0.001 | 0.70  | 0.299 |

11. The process of claim 10 wherein the crystalline molecular sieves have mole fractions of titanium, aluminum and phosphorus which are within the pentagonal compositional area defined by points a, b, c, d and e of the ternary diagram which is FIG. 2 of the drawings wherein a, b, c, d and e have the following values:

|       | Mole Fraction |       |       |
| Point | x     | y     | z     |
| ----- | ----- | ----- | ----- |
| a     | 0.002 | 0.499 | 0.499 |
| b     | 0.20  | 0.4   | 0.40  |
| c     | 0.20  | 0.5   | 0.30  |
| d     | 0.10  | 0.6   | 0.30  |
| e     | 0.002 | 0.6   | 0.398 |

12. The process of claim 10 wherein the molecular sieves have been calcined.

13. The process of claim 11 wherein the molecular sieves have been calcined.

14. Process for converting a hydrocarbon which comprises contacting said hydrocarbons under effective process conditions wherein the process is hydrocracking with at least one molecular sieve selected from the group consisting of crystalline molecular sieves comprising a composition expressed in terms of mole ratios of oxides in the anhydrous form as $$vR:pTiO_2:qAl_2O_3:rP_2O_5$$

wherein "R" represents at least one organic templating agent; "v" represents an effective amount of organic templating agent; "p", "q" and "r" represent moles, respectively, of TiO₂, Al₂O₃ and P₂O₅, based on said moles being such that they are within the pentagonal compositional area defined by points A, B, C, D and E of the ternary diagram which is FIG. 1 of the drawings said points A, B, C, D and E representing the following values for "p", "q" and "r":

|       | Moles |     |        |
|-------|-------|-----|--------|
| Point | p     | q   | r      |
| A     | 0.004 | 1.0 | 1.22   |
| B     | 176   | 1.0 | 11.0   |
| C     | 196   | 1.0 | 1.0    |
| D     | 0.828 | 1.0 | 0.0143 |
| E     | 0.003 | 1.0 | 0.427  |

15. The process of claim 14 wherein the molecular sieves have mole fractions of TiO₂, Al₂O₃ and P₂O₅ within the pentagonal compositional area defined by points a, b, c, d and e of the ternary diagram which is FIG. 2 of the drawings wherein a, b, c, d and e have the following values:

|       | Moles |     |       |
|-------|-------|-----|-------|
| Point | p     | q   | r     |
| a     | 0.008 | 1.0 | 1.0   |
| b     | 1.0   | 1.0 | 1.0   |
| c     | 0.80  | 1.0 | 0.65  |
| d     | 0.333 | 1.0 | 0.50  |
| e     | 0.67  | 1.0 | 0.663 |

16. The process of claim 14 wherein "v" has a value between zero and about 3.0.

17. The process of claim 11 or claim 12 wherein crystalline molecular sieves have the characteristic x-ray powder diffraction pattern set forth in any one of Tables A, C, E, G, M or O.

18. The process of claim 11 or claim 12 wherein such crystalline molecular sieves are calcined in air at a temperature between about 200° C. and about 700° C. for a period of time sufficient to remove at least a portion of template R.

19. Process for converting a hydrocarbon which comprises contacting said hydrocarbon under effective process conditions, wherein the process is a hydrotreating process with at least one crystalline molecular sieve selected from the group consisting of crystalline molecular sieves comprising pores having nominal diameters of greater than about 3 Angstroms and whose chemical composition in the as-synthesized and anhydrous form is represented by the unit empirical formula:

$$mR:(Ti_xAl_yP_z)O_2$$

wherein "R" represents at least one organic templating agent present in the intracrystalline pore system; "m" represents the moles of "R" present per mole of (Ti$_x$Al$_y$P$_z$)O₂ has a value of between zero and about 5.0; and "x", "y" and "z" represent the mole fractions of titanium, aluminum and phosphorus, respectively, present as tetrahederal oxides, said mole fractions being such that they are within the pentagonal compositional area defined by points A, B, C, D and E of the ternary diagram which is FIG. 1 of the drawings and points A, B, C, D and E representing the following values for "x", "y" and "z":

|       | Mole Fraction |      |       |
|-------|---------------|------|-------|
| Point | x             | y    | z     |
| A     | 0.001         | 0.45 | 0.549 |
| B     | 0.88          | 0.01 | 0.01  |
| C     | 0.98          | 0.01 | 0.01  |
| D     | 0.29          | 0.70 | 0.01  |
| E     | 0.001         | 0.70 | 0.299 |

20. The process of claim 19 wherein the crystalline molecular sieves have mole fractions of titanium, aluminum and phosphorus which are within the pentagonal compositional area defined by points a, b, c, d and e of the ternary diagram which is FIG. 2 of the drawings wherein a, b, c, d and e have the following values:

|       | Mole Fraction |       |       |
|-------|---------------|-------|-------|
| Point | x             | y     | z     |
| a     | 0.002         | 0.499 | 0.499 |
| b     | 0.20          | 0.4   | 0.40  |
| c     | 0.20          | 0.5   | 0.30  |
| d     | 0.10          | 0.6   | 0.30  |
| e     | 0.002         | 0.6   | 0.398 |

21. The process of claim 19 wherein the molecular sieves have been calcined.

22. The process of claim 20 wherein the molecular sieves have been calcined.

23. Process for converting a hydrocarbon which comprises contacting said hydrocarbons under effective process conditions wherein the process is hydrotreating with at least one molecular sieve selected from the group consisting of crystalline molecular sieves comprising a composition expressed in terms of mole ratios of oxides in the anhydrous form as $$vR:pTiO_2:qAl_2O_3:rP_2O_5$$

wherein "R" represents at least one organic templating agent; "v" represents an effective amount of organic templating agent; "p", "q" and "r" represent moles, respectively, of TiO₂, Al₂O₃ and P₂O₅, based on said moles being such that they are within the pentagonal compositional area defined by points A, B, C, D and E of the ternary diagram which is FIG. 1 of the drawings said points A, B, C, D and E representing the following values for "p", "q" and "r":

|       | Moles |     |        |
|-------|-------|-----|--------|
| Point | p     | q   | r      |
| A     | 0.004 | 1.0 | 1.22   |
| B     | 176   | 1.0 | 11.0   |
| C     | 196   | 1.0 | 1.0    |
| D     | 0.828 | 1.0 | 0.0143 |
| E     | 0.003 | 1.0 | 0.427  |

24. The process of claim 23 wherein the molecular sieves have mole fractions of TiO₂, Al₂O₃ and P₂O₅ within the pentagonal compositional area defined by points a, b, c, d and e of the ternary diagram which is FIG. 2 of the drawings wherein a, b, c, d and e have the following values:

|       | Moles |     |     |
|-------|-------|-----|-----|
| Point | p     | q   | r   |
| a     | 0.008 | 1.0 | 1.0 |

-continued

| Point | Moles | | |
|---|---|---|---|
| | p | q | r |
| b | 1.0 | 1.0 | 1.0 |
| c | 0.80 | 1.0 | 0.65 |
| d | 0.333 | 1.0 | 0.50 |
| e | 0.67 | 1.0 | 0.663. |

25. The process of claim 23 wherein "v" has a value between zero and about 3.0.

26. The process of claim 20 or claim 21 wherein crystalline molecular sieves have the characteristic x-ray powder diffraction pattern set forth in any one of Tables A, C, E, G, M or O.

27. The process of claim 20 or claim 21 wherein such crystalline molecular sieves are calcined in air at a temperature between about 200° C. and about 700° C. for a period of time sufficient to remove at least a portion of template R.

* * * * *